(12) United States Patent
Mische

(10) Patent No.: US 9,351,772 B2
(45) Date of Patent: May 31, 2016

(54) METHOD AND DEVICES FOR THE TREATMENT OF NASAL SINUS DISORDERS

(76) Inventor: Hans A. Mische, Grey Eagle, MN (US)

( * ) Notice: Subject to any disclaimer, the term of this patent is extended or adjusted under 35 U.S.C. 154(b) by 1994 days.

(21) Appl. No.: 12/011,115

(22) Filed: Jan. 23, 2008

(65) Prior Publication Data

US 2008/0125805 A1 May 29, 2008

Related U.S. Application Data

(63) Continuation-in-part of application No. 09/733,775, filed on Dec. 8, 2000, now Pat. No. 8,007,498, and a continuation-in-part of application No. 11/986,939, filed on Nov. 26, 2007, which is a continuation-in-part of application No. 11/504,514, filed on Aug. 14, 2006, now abandoned, which is a continuation-in-part of application No. 10/843,828, filed on May 11, 2004, now Pat. No. 7,300,449, which is a continuation-in-part of application No. 10/056,323, filed on Jan. 24, 2002, now Pat. No. 6,764,498, which is a continuation-in-part of application No. 09/457,971, filed on Dec. 9, 1999, now Pat. No. 6,375,666.

(60) Provisional application No. 60/169,778, filed on Dec. 9, 1999, provisional application No. 60/181,651, filed on Feb. 10, 2000, provisional application No. 60/191,664, filed on Mar. 23, 2000, provisional application No. 60/982,931, filed on Oct. 26, 2007.

(51) Int. Cl.
| | | |
|---|---|---|
| A61M 29/00 | (2006.01) |
| A61F 2/46 | (2006.01) |
| A61B 17/72 | (2006.01) |
| A61B 17/68 | (2006.01) |
| A61B 17/00 | (2006.01) |
| A61F 2/28 | (2006.01) |
| A61M 25/10 | (2013.01) |

(52) U.S. Cl.
CPC ............ *A61B 17/7258* (2013.01); *A61B 17/68* (2013.01); *A61B 2017/00557* (2013.01); *A61B 2017/00867* (2013.01); *A61F 2002/2821* (2013.01); *A61M 25/10* (2013.01); *A61M 25/104* (2013.01); *A61M 2025/1068* (2013.01); *A61M 2210/02* (2013.01)

(58) Field of Classification Search
CPC ........... A61B 17/8852; A61B 17/8855; A61B 17/8858; A61B 17/7044
USPC ......... 606/191–198, 86 R; 128/898; 623/1.15
See application file for complete search history.

(56) References Cited

U.S. PATENT DOCUMENTS

| | | | |
|---|---|---|---|
| 3,710,789 A | 1/1973 | Ersek | |
| 3,800,788 A | * 4/1974 | White | ........................ 606/86 R |
| 4,627,434 A | 12/1986 | Murray | |

(Continued)

FOREIGN PATENT DOCUMENTS

| | | | | |
|---|---|---|---|---|
| EP | 0819413 A2 | 1/1998 | | |
| WO | WO99/02214 | * 1/1999 | ............ A61M 25/00 |

*Primary Examiner* — Tuan V Nguyen
(74) *Attorney, Agent, or Firm* — Kinney & Lange, P.A.

(57) ABSTRACT

Methods and devices for facilitating the treatment and repair of nasal sinus afflictions utilizing devices that are positioned within proximity of the nasal sinus and the afflicted location. The methods and devices are particularly beneficial for the treatment of sinusitis, broken noses, sleep apnea, cleft palates and deviated septums. In addition, the devices may enhance and expedite patient recovery and reduce or mitigate bleeding.

17 Claims, 29 Drawing Sheets

(56) References Cited

U.S. PATENT DOCUMENTS

| | | | |
|---|---|---|---|
| 4,969,888 A | 11/1990 | Scholten et al. | |
| 5,634,946 A * | 6/1997 | Slepian | 128/898 |
| 5,741,270 A | 4/1998 | Hansen et al. | |
| 6,127,597 A * | 10/2000 | Beyar et al. | 606/86 R |
| 6,168,616 B1 | 1/2001 | Brown, III | |
| 6,248,110 B1 | 6/2001 | Reiley et al. | |
| 6,281,262 B1 * | 8/2001 | Shikinami | 523/105 |
| 6,491,940 B1 * | 12/2002 | Levin | 424/434 |
| 7,361,168 B2 * | 4/2008 | Makower et al. | 604/509 |
| 7,780,730 B2 | 8/2010 | Saidi | |
| H0002260 H * | 7/2011 | Toleikis | 424/423 |
| 2001/0018583 A1 * | 8/2001 | Bays | 604/516 |
| 2005/0137611 A1 * | 6/2005 | Escudero et al. | 606/108 |
| 2005/0240147 A1 * | 10/2005 | Makower et al. | 604/96.01 |
| 2005/0245906 A1 * | 11/2005 | Makower et al. | 604/891.1 |
| 2007/0005094 A1 * | 1/2007 | Eaton et al. | 606/199 |
| 2007/0250105 A1 | 10/2007 | Ressemann et al. | |

* cited by examiner

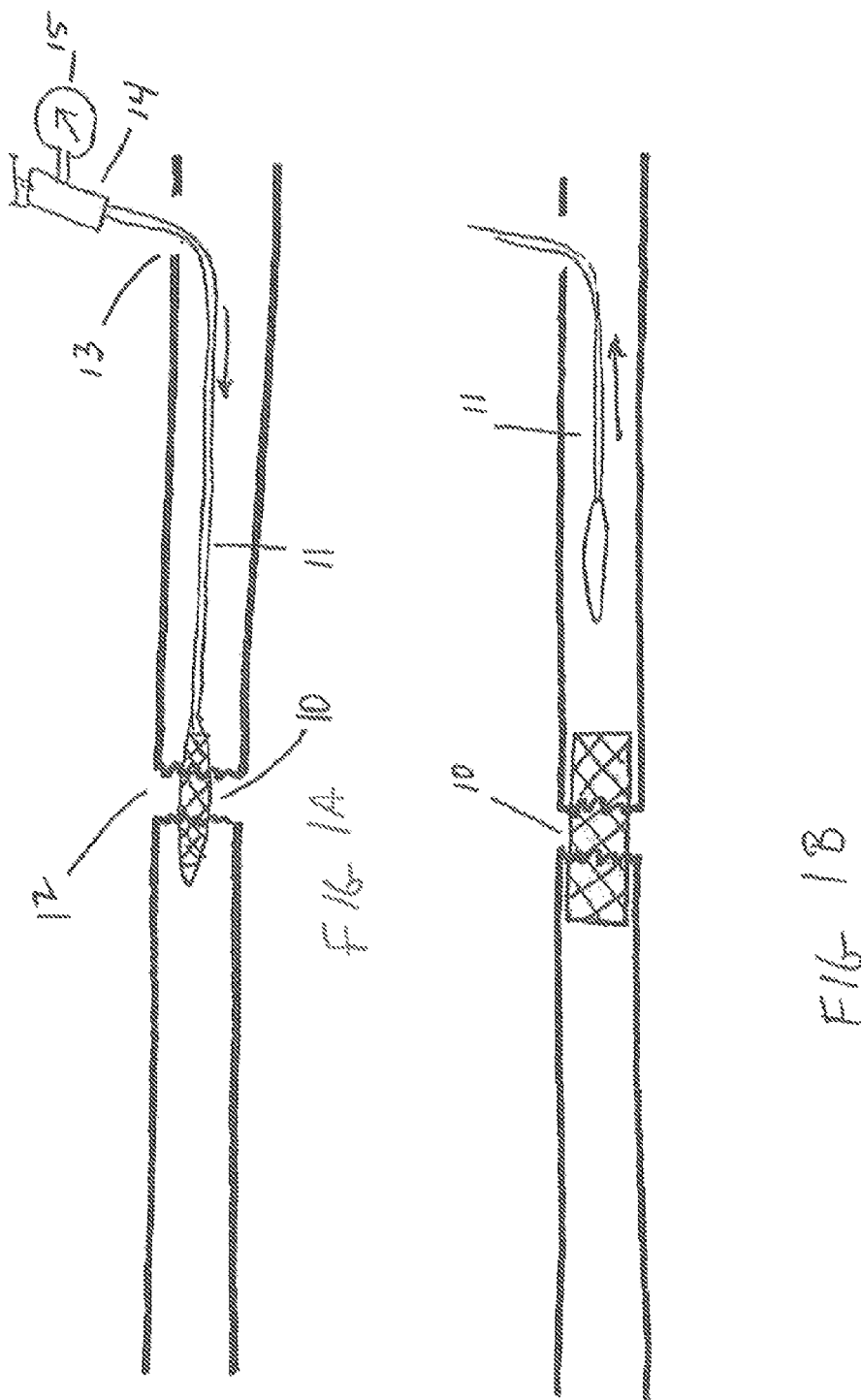

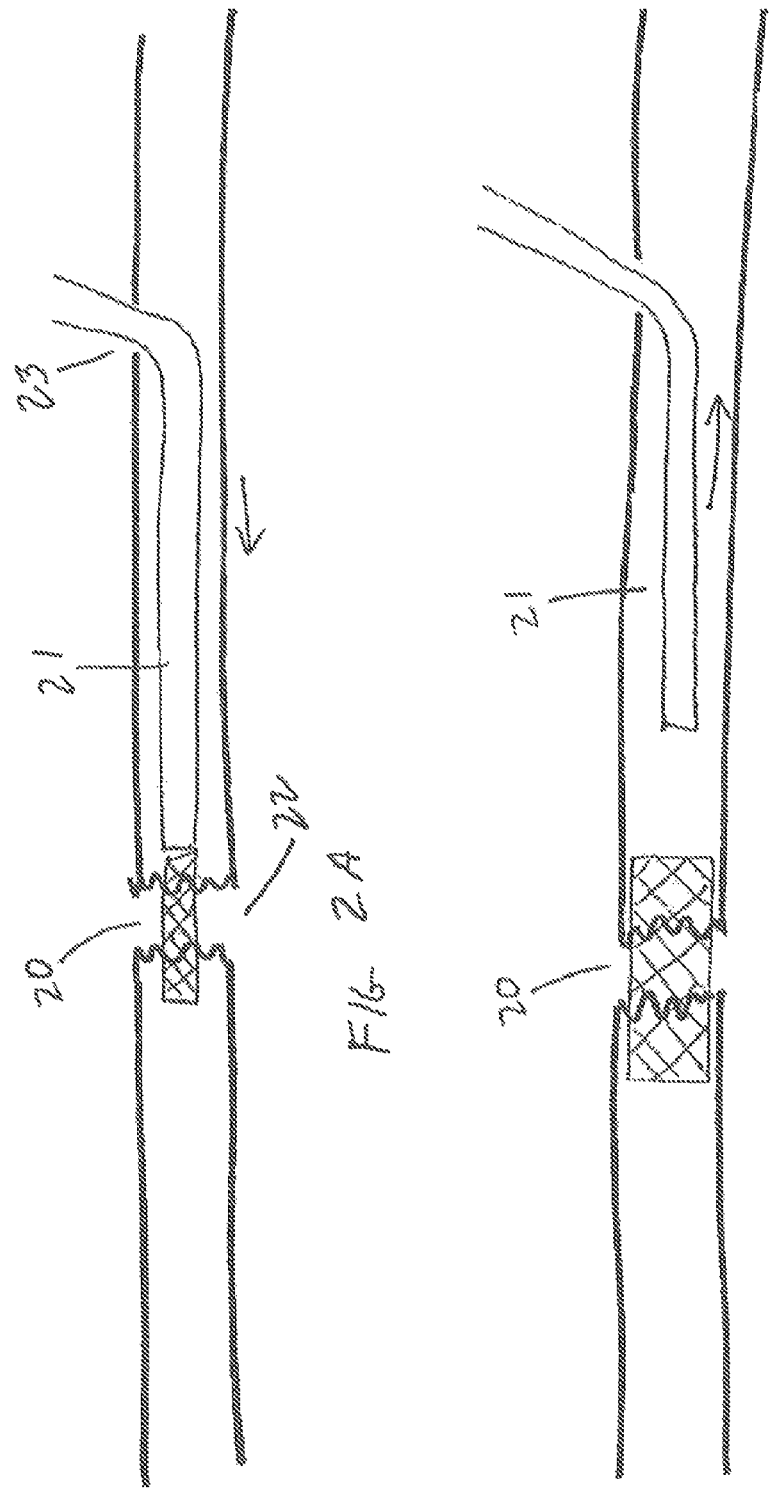

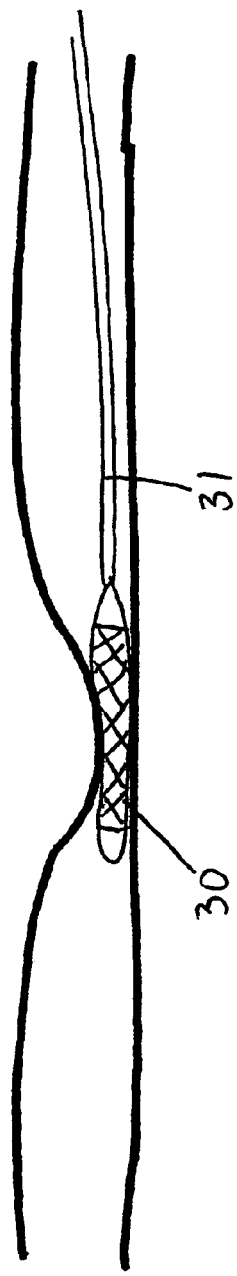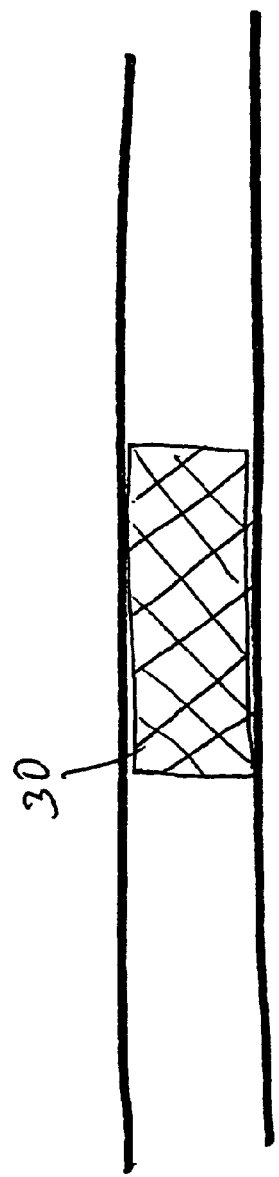

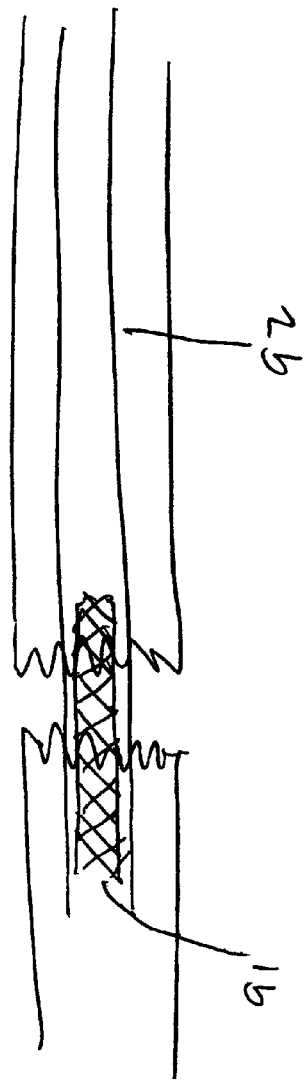
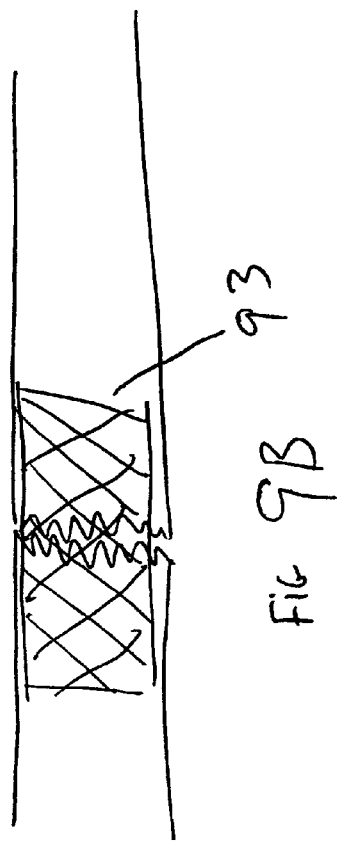
Fig 9A
Fig 9B

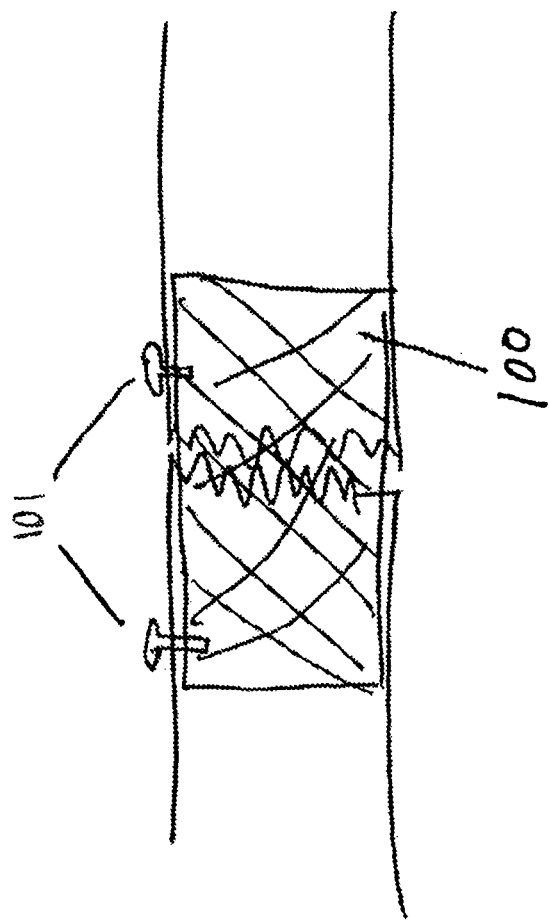

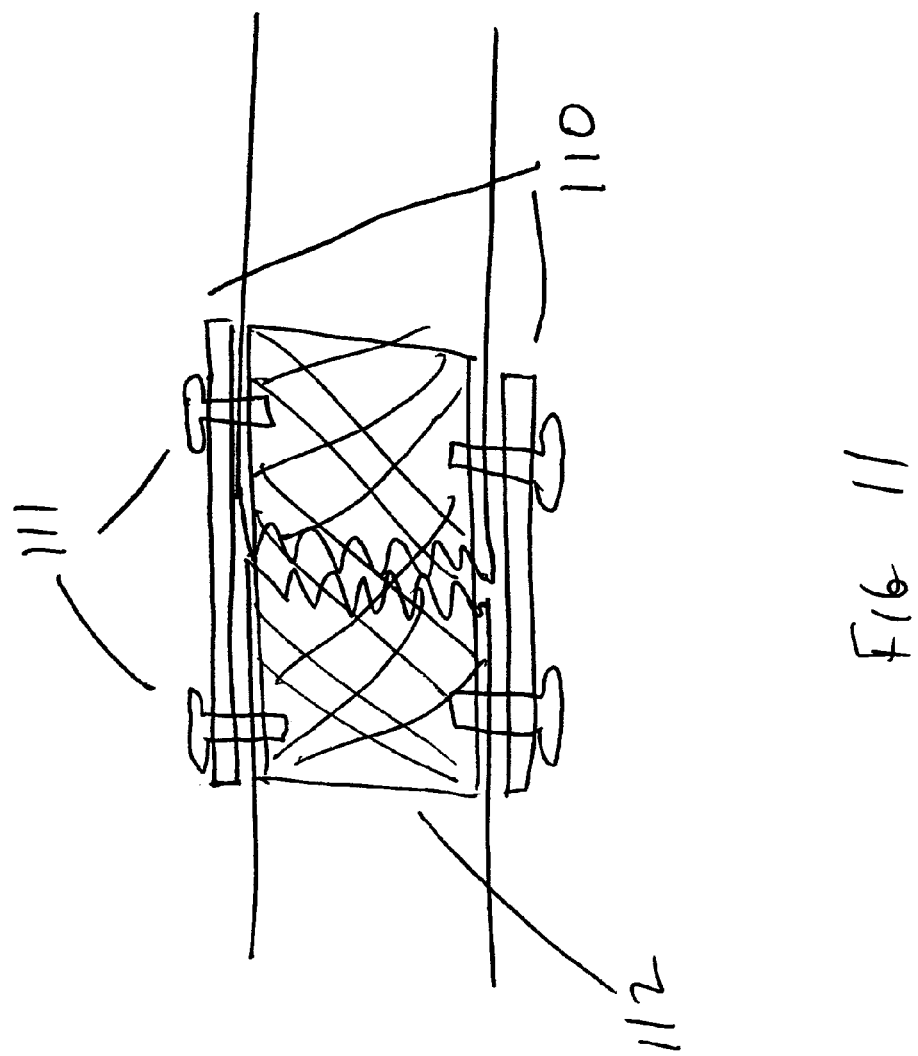

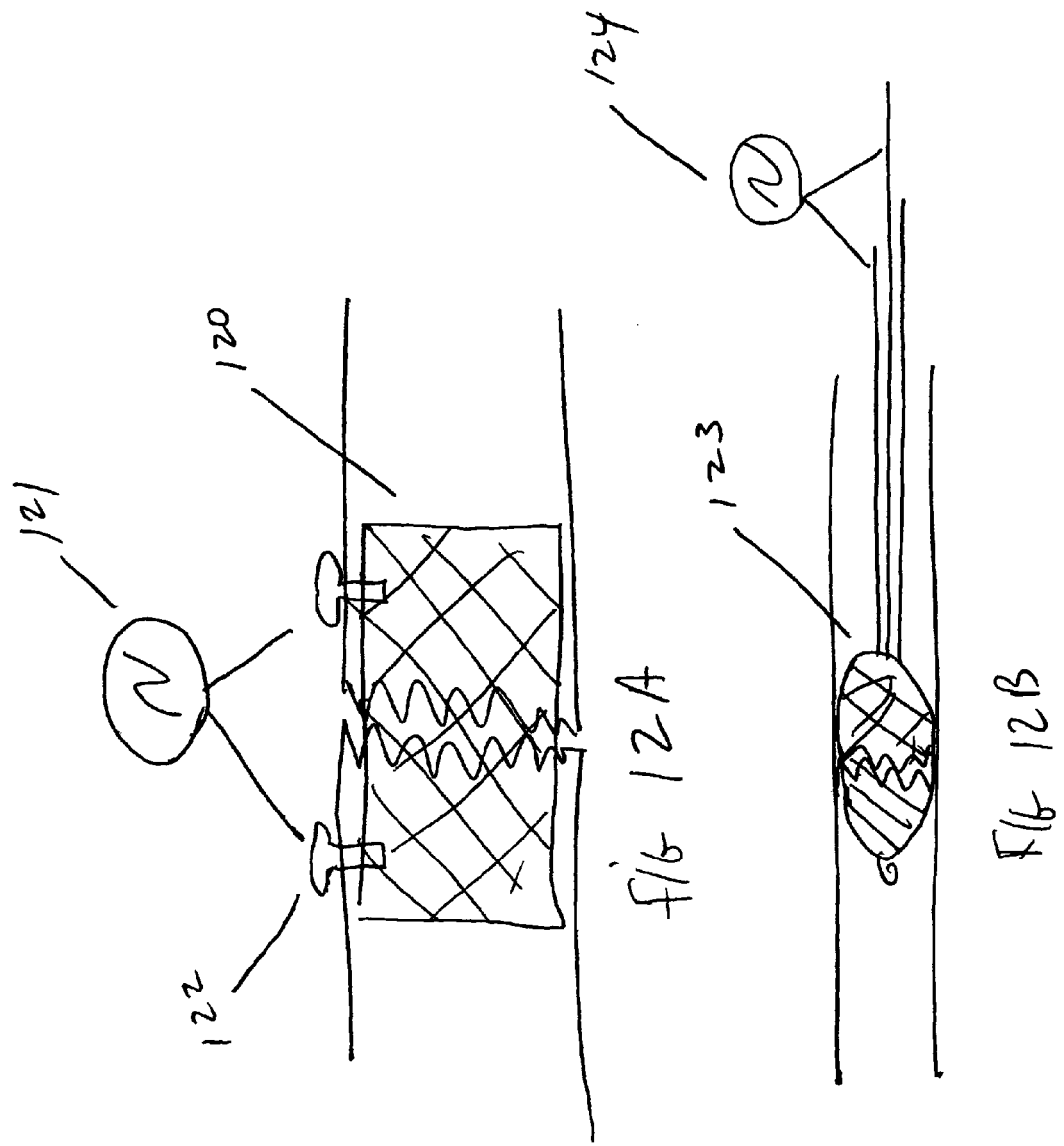

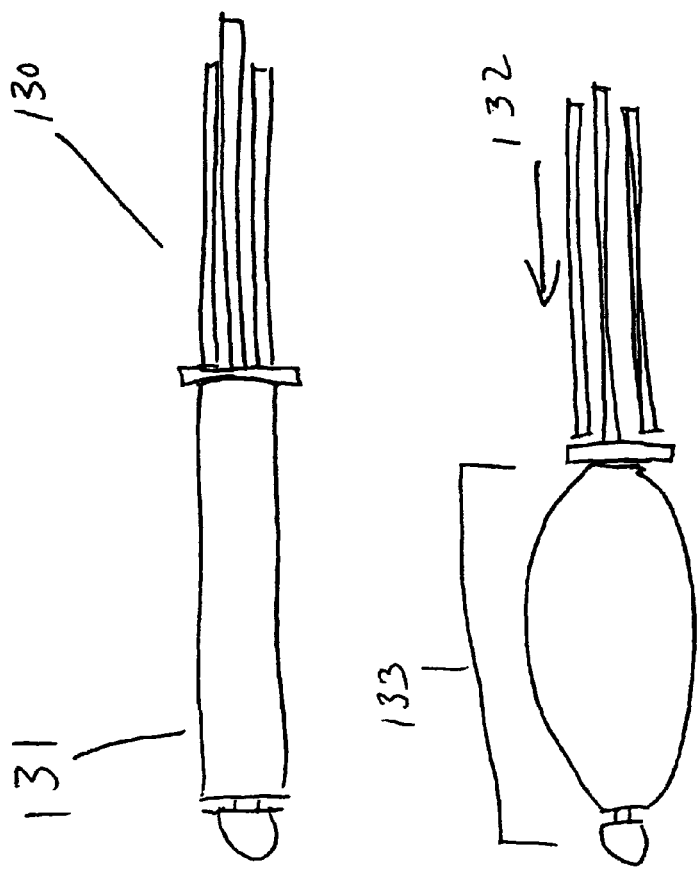

METHOD AND DEVICES FOR THE TREATMENT OF NASAL SINUS DISORDERS

CROSS REFERENCE TO RELATED APPLICATION

This application claims the benefit of the following U.S. Provisional applications: All of which are incorporated herein by reference in their entirety: U.S. Provisional Application having Ser. No. 60/169,778 filed on Dec. 9, 1999, U.S. Provisional Application having Ser. No. 60/181,651 filed on Feb. 10, 2000, U.S. Provisional Application having Ser. No. 60/191,664 filed on Mar. 23, 2000, U.S. Provisional Application having Ser. No. 60/982,931 filed on Oct. 26, 2007, and is a continuation-in-part of U.S. patent application having Ser. No. 09/733,775 filed on Dec. 8, 2000 entitled "Methods and Devices for Treatment of Bone Fractures".

In addition, this application herein claims priority to and incorporates by reference in their entirety the following: U.S. Pat. No. 6,375,666 filed Dec. 9, 1999 entitled "Methods and Devices for the Treatment of Neurological Disorders", U.S. Pat. No. 6,764,498 filed Jan. 24, 2002 entitled "Methods and Devices for the Treatment of Neurological Disorders", U.S. Pat. No. 7,300,449 filed May 11, 2004 entitled "Methods and Devices for the Treatment of Neurological and Physiological Disorders", U.S. patent application Ser. No. 11/504,514 filed on Aug. 14, 2006 entitled "Methods and Devices for the Treatment of Neurological and Physiological Disorders", and U.S. patent application Ser. No. 11/986,939 filed on Nov. 26, 2007 entitled "Methods and Devices for the Treating Obesity, Incontinence, and Neurological and Physiological Disorders".

FIELD OF THE INVENTION

The present invention relates generally to inventive medical devices and methods and more particularly to minimally invasive, catheter based devices, systems and method for treating sinusitis and other ear, nose & throat disorders.

BACKGROUND OF THE INVENTION

The current methods of treating bone fractures ranges from simple setting of the bone and constraining motion via a cast or wrap to using pins, screws, rods and cement to fixate fracture site. With the use of casts, the bone is not stabilized and misalignment may occur after placing the cast. This may require the cast to be removed and the bone reset. This is a very uncomfortable and painful procedure for the victim and can ultimately result in permanent misalignment of the healed bone. The treatment modalities requiring a surgical procedure are painful and are associated with a high rate of complications. Post-procedural infections are one of the major complications associated with these surgical procedures. Many of these infections result in necrosis of bone and tissue and require additional surgical interventions and therapy. The invention discussed here provides for a unique and novel means of treating a variety of bone fractures with minimally invasive techniques and low complication rates. In addition, as further discussed, this invention also provides for methods and devices for the treatment of nasal sinus disorders and maladies. A number of therapies are available for treating nasal sinus disorders such as sinusitis, deviated septums, allergies, and infections. Drugs, surgery, and devices are used commonly to attempt to treat or alleviate these afflictions. This invention uses devices, device-based systems and delivery systems to provide improved acute and long-term therapies. The nose, nose structures and its associated nasal sinuses suffer many afflictions that manifest into painful and uncomfortable situations for the owner of the nose. Some of these inflictions include sinusitis, deviated septums, allergies, broken noses, and infections. Sinusitis is infection or inflammation of the mucous membranes that line the inside of the nose and sinuses. Sinuses are hollow spaces, or cavities, located around your eyes, cheeks, and nose. FIG. 14 shows the paranasal sinuses. Paranasal sinuses are air-filled spaces, communicating with the nasal cavity, within the bones of the skull and face. The paranasal sinuses are joined to the nasal cavity via small orifices called ostia. These become blocked relatively easily by allergic inflammation, or by swelling in the nasal lining which occurs with a cold. If this happens, normal drainage of mucus within the sinuses is disrupted, and sinusitis may occur. Humans possess a number of paranasal sinuses, divided into subgroups that are named according to the bones within which the sinuses lie:

the maxillary sinuses (MF), also called the maxillary antra and the largest of the paranasal sinuses, are under the eyes, in the maxillary bones (cheek bones).

the frontal sinuses (FS), over the eyes, in the frontal bone, which forms the hard part of the forehead.

the ethmoid sinuses (ES), which are formed from several discrete air cells within the ethmoid bone between the nose and the eyes.

the sphenoid sinuses, in the sphenoid bone at the center of the skull base under the pituitary gland.

The paranasal sinuses are not the only sinuses within the skull: the mastoid cells in the mastoid bone around the middle ear are also a type of sinus.

When a mucous membrane becomes inflamed, it swells, blocking the drainage of fluid from the sinuses into the nose and throat, which causes pressure and pain in the sinuses. Bacteria and fungus are more likely to grow in sinuses that are unable to drain properly. Bacterial or fungal infections in the sinuses often cause more inflammation and pain, and they are more likely to last longer, worsen with time, and become chronic. While colds usually trigger this process, any factor that causes the mucous membrane to become inflamed may lead to sinusitis. Many people with nasal allergies (allergic rhinitis), are likely to have recurring or long-term (chronic) sinus infections. Nasal polyps and structural problems in the nose such as a deviated septum, and other conditions can also block the nasal passages, increasing the risk of developing sinusitis.

Sinuses can become blocked during a viral infection such as a cold, and sinus inflammation and infection can develop as a result. One key distinction between a cold and sinusitis is that cold symptoms, including a stuffy nose, begin to improve within 5 to 7 days. Sinusitis symptoms last longer and get worse after 7 days. There are two types of sinusitis: acute (sudden) and chronic (long-term). Acute (sudden) sinusitis is usually caused by a viral infection and often develops rapidly. It usually lasts for 4 weeks or less, and the symptoms often begin to clear up within a week without any treatment Acute sinusitis caused by a bacterial infection is less likely to clear up on its own and may lead to chronic sinusitis or to complications in which the infection spreads beyond the sinuses. Nasal discharge that contains pus and worsens after 5 days or persists for more than 10 days is usually a strong sign of acute sinusitis caused by a bacterial infection. With chronic sinusitis, the sufferers always have a low level of sinusitis symptoms. Chronic sinusitis can lead to permanent changes in the mucous membranes that line the sinuses and may make you more prone to sinus infections. The main symptoms of sinusitis are a runny or stuffy nose and facial pain and pressure. A yellow or greenish discharge from the nose or down the back of the throat (postnasal discharge). The location of pain and tenderness depends on which sinus is affected. The location of pain and tenderness may depend on which sinus is affected; Pain over the cheeks and upper teeth is often caused by maxillary sinus inflammation; Pain in the forehead, above the eyebrow, may be caused by frontal sinus inflammation; Pain behind the eyes, on top of the head, or in both temples may be caused by sphenoid sinus inflammation; Pain around or behind the eyes is caused by ethmoid sinus inflammation.

Other common symptoms of sinusitis may include, headache, bad breath, runny or stuffy nose, cough that produces mucus, fever, tooth pain, reduced sense of taste or smell, post-nasal drainage or drip. Sinusitis often improves on its own, but it may need to be treated with antibiotics or other medications, depending on the severity and duration of symptoms. With chronic sinusitis, a longer course of medications is often needed. Surgery may be required if the sufferers have taken antibiotics and other medications for an extended period of time but still have symptoms, or when complications (such as the spread of infection beyond the sinuses) are likely. Fungal infections, which account for a significant number of chronic sinusitis cases, do not respond to antibiotic treatment. They may require treatment with antifungal medications, corticosteroids, or surgery. Chronic sinusitis may last 3 to 8 weeks or longer and usually requires 3 to 4 weeks of antibiotic treatment. Symptoms may persist or return despite adequate antibiotic treatment. A different antibiotic may be needed to treat the infection. Referral to an ear, nose, and throat (ENT) specialist (also called an otolaryngologist) may be necessary if symptoms of sinusitis do not go away despite long-term antibiotic treatment.

Medications are used and sometimes combined to treat sinusitis. Antibiotics kill bacteria. A few examples of antibiotics used are amoxicillin (Amoxil, Larotid, Trimox), cefaclor (Ceclor), and telithromycin (Ketek). Decongestants reduce the swelling of the mucous membranes in the nose. Some examples may include oxymetazoline hydrochloride (Afrin) and phenylephrine hydrochloride (Neo-Synephrine, Sinex Decongestant Nasal Spray). Analgesics, such as aspirin, acetaminophen or ibuprofen, are used to relieve pain. Corticosteroids, such as beclomethasone dipropionate (Beconase, Vancenase) or prednisone (Deltasone, Prednicen-M), reduce inflammation in the nasal passages and may be given as an inhaled nasal spray. Mucolytics, such as guaifenesin (Robitussin), are used to thin the mucus Current sinus treatment options Include the following:
Functional Endoscopic Sinus Surgery (FESS):

FESS involves the insertion of the endoscope, a very thin fiber-optic tube, into the nose for a direct visual examination of the openings into the sinuses. With state of the art microtelescopes and instruments, abnormal and obstructive tissues are then removed. In the majority of cases, the surgical procedure is performed entirely through the nostrils, leaving no external scars. There is little swelling and only mild discomfort.

The advantage of the procedure is that the surgery is less extensive, there is often less removal of normal tissues, and can frequently be performed on an outpatient basis. After the operation, the patient will sometimes have nasal packing. Ten days after the procedure, nasal irrigation may be recommended to prevent crusting.

Image guided surgery: The sinuses are physically close to the brain, the eye, and major arteries, always areas of concern when a fiber optic tube is inserted into the sinus region. The growing use of a new technology, image guided endoscopic surgery, is alleviating that concern. This type of surgery may be recommended for severe forms of chronic sinusitis, in cases when previous sinus surgery has altered anatomical landmarks, or where a patients sinus anatomy is very unusual, making typical surgery difficult.

Image guidance is a near-three-dimensional mapping system that combines computed tomography (CT) scans and real-time information about the exact position of surgical instruments using infrared signals. In this way, surgeons can navigate their surgical instruments through complex sinus passages and provide surgical relief more precisely.

Another option is the Caldwell-Luc operation, which relieves chronic sinusitis by improving the drainage of the maxillary sinus, one of the cavities beneath the eye. The maxillary sinus is entered through the upper jaw above one of the second molar teeth. A "window" is created to connect the maxillary sinus with the nose, thus improving drainage. The operation is named after American physician George Caldwell and French laryngologist Henry Luc and is most often performed when a malignancy is present in the sinus cavity.

Other imaging technologies can be used as well. For example magnetic resonance imaging or forms or x-ray and fluoroscopy.

Surgery on the nasal septum, turbinates, and sinuses is recommended only after it has been determined that medical management has been unsuccessful. While these procedures are generally very successful, patients must be aware of certain risks before electing to proceed. These risks include, but are not necessarily limited to, the following:

Postoperative Bleeding:

Aspirin, ibuprofen and certain non-prescription supplements (vitamin E, garlic, etc.) can increase the propensity to bleed, so patients should consult with their physicians before using these agents before or after surgery. Intranasal packing is utilized by many sinus surgeons to help avoid this complication but occasionally postoperative bleeding is encountered despite all precautions.

Anesthesia Complications:

Adverse reactions to local or general anesthesia may occur, including cardiac and pulmonary complications. Fortunately, these risks are quite rare in this era of modern anesthesia.

Intracranial Complications:

The base of the skull forms the roof of the ethmoid and sphenoid sinuses. If this layer is violated, a leak of cerebrospinal fluid (the fluid that bathes the brain and spinal cord) may occur (FIG. 1). This can usually be repaired at the time of the initial surgery, although in rare cases further complications such as meningitis may ensue.

Intraorbital Complications:

The orbit is situated immediately adjacent to several of the paranasal sinuses but is separated by a layer of bone. Because of this close proximity, in rare cases bleeding may occur into the orbit requiring repair at the time of the initial surgery. Visual loss and blindness have been reported but are extremely rare.

Smell:

The sense of smell usually improves, although it may occasionally worsen, depending on the extent of infection, allergy or polyps.

Voice Changes:

One of the functions of the sinuses is to affect resonance, so vocal professionals should be aware of potential changes in their voice after sinus surgery. Infection: The most common reason to undergo sinus surgery is a chronic infection that does not resolve with medications. The patient with sinusitis is therefore at risk of developing certain other infections in this area (abscesses, meningitis, etc.) regardless of whether they manage the sinusitis with or without surgery.

Nasal Obstruction:

Much of the nasal septum is made of cartilage, which has "memory"—the propensity to move back to its original position. Despite certain measures performed by the surgeon at the time of septoplasty this may still occur and require a secondary procedure. Small scar bands may also occur in the nose and require removal by the surgeon at postoperative visits.

Numbness:

A transient numbness of the front upper teeth, lip or nose may occur after surgery but is usually self-limiting.

While surgery may entail these complications, it is also crucial to remember that the failure to intervene may also place the patient at risk for certain complications. When left untreated, the infection may rarely spread to adjacent structures such as the eye or brain and lead to abscesses in these areas, meningitis, visual loss, or even death.

As aforementioned background, there are a number of treatments for sinusitis and other nasal sinus maladies. However, there is a need for more effective methods and devices for the treatment of these ailments.

SUMMARY OF THE INVENTION

In contrast to the prior art, the present invention proposes treatment of bone fractures using minimally invasive techniques, methods, equipment and devices to position and deliver an expandable fracture fixating device into the medullary cavity (marrow conduit). The device is preferably an expandable structure that "bridges" the fracture site and fixates the site upon expansion. In addition to fixation, the device also joins the fractured bone such as in the case of a compound fracture. Referring to the device as a bridge, the BRIDGE is substantially hollow and has low surface area and mass, the majority of bone marrow volume can be preserved. The ability to preserve a large quantity of the bone marrow cavity is beneficial for healing, bone health and maintaining the body's natural ability to generate red blood cells. In addition, the stress applied to the bone by the expanded or expanding "BRIDGE" facilitates rapid bone growth and strength. The operable level of stress applied to the bone will vary from low levels to high levels dependent on the type, size and location of bone to be treated. It is also envisioned that the BRIDGE can be used to expand and support bones that are crushed or compressed. The BRIDGE can be delivered by a variety of expansion devices, can be self expanding to due to inherent spring forces within the BRIDGE structure, or can be expansively actuated utilizing elements and mechanisms within the BRIDGE structure. These various devices and alternative embodiments will be detailed further.

Although standard medical equipment may be used to facilitate the procedure, it may be necessary to design unique, specialized tools in order for this invention to be properly utilized. These devices may include tissue separators, retractors, drills, introducers, coring tools, and others.

The invention is disclosed in the context of treating bone fractures but other organs and anatomical tissues are contemplated as well. For example, the invention may be used to treat spinal stenosis, individual vertebrae, and support or fixate segments of the spinal column. Likewise, a broken nose, sinus cavity or collapsed lung can be supported using this invention. Pelvic fractures in females could also benefit from placing this device within the vaginal cavity in order to support and fixate the pelvis or pubic bone. Additionally, the invention may also be used in the treatment of sleep apnea and its associated complications.

The invention discloses and teaches methods and devices equal to or similar to those in U.S. Provisional application having Ser. No. 60/169,778 filed on Dec. 9, 1999, U.S. Provisional application having Ser. No. 60/181,651 filed on Feb. 10, 2000, U.S. Provisional application having Ser. No. 60/191,664 filed on Mar. 23, 2000, and U.S. patent application having Ser. No. 09/733,775 filed on Dec. 8, 2000 entitled "Methods and Devices for Treatment of Bone Fractures, all invented by Mische, the inventor of this immediate invention. In addition to treating bone fractures, these documented inventions disclose and teach the use of novel devices and methods for the treatment and support of nasal sinuses. In addition, U.S. Pat. No. 6,375,666 and its continuing applications by Mische, disclose similar devices positioned within the frontal sinus. Therefore, the following inventions by Mische elaborate further on the previous inventions by Mische. Therefore, the Mische references made available have been teaching resources for those skilled in the art the following methods and devices which are being claimed.

Therefore, the present invention proposes treatment bone fractures, and various sinus and nasal ailments using minimally invasive techniques, methods, equipment and devices to position and deliver therapeutic devices within the bones, sinus cavities, and nasal cavities. These inventions will be summarized in greater detail in the following discussion and disclosures.

In an initial aspect of the invention, a method of treating a constricted sinus passageway of a patient includes creating an access hole in a bone structure of the patient so as to form a passageway to a sinus cavity. An elongate member having an inflation member thereon (e.g., a balloon) is inserted through the passageway. The inflation member is positioned within the constricted sinus passageway. The inflation member is then expanded so as to expand and dilate at least a portion of the constricted sinus passageway.

In one embodiment, the device is an expandable tubular device that is advanced into the sinus or nasal cavities on a minimally invasive delivery device and expanded at the site of an occlusion of the targeted cavity.

In another embodiment, the expandable tubular device is of a self-expandable design that expands at the desired location of the cavity when released by the delivery device.

In yet another embodiment, the tubular device is a balloon-expandable design that is expanded by a delivery device having an inflatable balloon portion.

In yet another embodiment, the tubular device is an expandable design that is expanded by a delivery device having an expandable grommet portion.

In another embodiment, the method of treatment includes the simultaneous use of an endoscope in order to visualize proper placement of the therapeutic device.

In another embodiment, the delivery device may incorporate endoscopic means to assist in contemporaneous real-time imaging and treatment.

In still another embodiment, the method of treatment includes advancing the delivery device into the cavities through the nose. The delivery device is advanced over a guiding device such as a guide wire.

In still another embodiment, the method of treatment includes advancing the delivery device into the cavities through the nose. The delivery device is advanced through a guiding device such as a guiding catheter or cannula.

In another embodiment, the treatment method includes the use of a device that has an expandable treatment element that, when activated at the proper location, dilates the obstructed cavity.

In another embodiment, the expandable treatment element is an inflatable balloon that is in fluid connection via a lumen in the delivery device to an inflation device (e.g. syringe).

In another embodiment, the tubular device has a coating on the exterior surface which adds in facilitating hemostasis.

In another embodiment, the tubular device has a coating on the exterior surface that incorporates drugs, antibiotics, and other agents that release into the lining of the cavity.

In another embodiment, the tubular device has a coating on the interior surface that incorporates drugs, antibiotics, and other agents that release into the lining of the cavity.

In another embodiment, the tubular device is capable of absorbing therapeutic substances and compounds drugs, antibiotics, and other agents that release into the lining of the cavity.

In another embodiment, the tubular device is capable of absorbing therapeutic medicants such as drugs, antibiotics, and other agents after being placed within the sinus or nasal cavity. These medicants can be introduced via sprays, mists, vapors or fluids that are absorbed into or on the tubular device when injected or inhaled.

In another embodiment, the tubular device allows for the passage of air during respiratory inhalation and exhalation.

In another embodiment, the tubular device has a one-way valve that only allows for exhalation of air and drainage of fluids. This is important so as to prevent inhaling air or contaminants that may cause infection, irritation, or congestion.

In another embodiment, the tubular device has a one-way valve that only allows for inhalation.

In another embodiment, the tubular device has an air filtering element that prevents detrimental substances from entering the sinus. The filter can be removed and replaced alone, or the entire tubular device can be removed and replaced as needed.

In another embodiment, the tubular device spans a fistula between sinus cavities.

In another embodiment, the tubular device spans a fistula between the sinus and brain cavities.

In another embodiment, the tubular device spans a fistula between sinus and orbital cavities.

In another embodiment, the tubular device is connected to an RF generator to cauterize the lining of the cavity.

In another embodiment, a braided the tubular device can be retrieved or removed from the cavity by pulling on one end of the device, which causes the device to contract diametrically.

In yet another embodiment, a coiled tubular device can be retrieved or removed from the cavity by pulling on one end of the device, which causes the device to unravel as it is removed from the sinus.

In another preferred embodiment, method of treatment consists of advancing a self-expanding tubular device with delivery system to the treatment site within the sinus, and releasing the self-expanding tubular device at the treatment site.

In another embodiment, a device can be retrieved or removed from the cavity by heating or cooling the device, which causes the device to contract diametrically.

In another embodiment, the delivery system utilizes endoscopic technology to facilitate diagnosis and to assist in treatment.

In another embodiment, the treatment system utilizes endoscopic technology to facilitate diagnosis and to assist in positioning the treatment element.

In another embodiment, the expandable device has cutting surfaces or elements that facilitate the dilation of cavities, as well as patterning and controlling scar tissue formation.

In another embodiment, the implanted Bridge is made of biodegradable materials. These biodegradable materials can have therapeutics additives agents incorporated into the structure.

In another embodiment, the Bridge is used in septoplasty and rhinoplasty procedures to overcome and make more normal the anatomical malformations of the nose and its associated structures In another embodiment, the Bridge is used to maintain patency of the straight sinus, superior sagittal, sigmoid sinus, petrosquamous sinus, transverse sinus and other sinus within the head.

In another embodiment of the invention, a method of treating a constricted sinus passageway of a patient includes traversing the external bone of the skull wall of the patient so as to form a passageway to the frontal sinus cavity and inserting an elongate member through the passageway, the elongate member having an inflation member disposed thereon. The inflation member is positioned within the constricted sinus passageway and the inflation member is expanded so as to expand at least a portion of the constricted sinus passageway.

In another embodiment of the invention, a method of treating a constricted sinus passageway of a patient includes traversing the external bone of the skull wall of the patient so as to form a passageway to the frontal sinus cavity and inserting an elongate member through the passageway, the elongate member having an inflation member disposed thereon, upon which is disposed an expandable tubular element. The inflation member is positioned within the constricted sinus passageway and the inflation member is expanded so as to expand the tubular element and subsequently at least a portion of the constricted sinus passageway.

In another embodiment of the invention, a method of treating a constricted sinus passageway of a patient includes traversing a sinus wall of the patient so as to form a passageway into an adjacent sinus cavity and inserting an elongate member through the passageway, the elongate member having an inflation member disposed thereon. The inflation member is positioned within the constricted sinus passageway and the inflation member is expanded so as to expand at least a portion of the constricted sinus passageway.

In another embodiment of the invention, a method of treating a constricted sinus passageway of a patient includes traversing a sinus wall of the patient so as to form a passageway into an adjacent sinus cavity and inserting an elongate member through the passageway, the elongate member having an inflation member disposed thereon, upon which is disposed an expandable tubular element. The inflation member is positioned within the constricted sinus passageway and the inflation member is expanded so as to expand the tubular element and subsequently at least a portion of the constricted sinus passageway.

In another embodiment, access to the target sinus cavity is attained by creating an access port through a tooth, through the tooth socket, and into the sinus.

In another embodiment, access to the target sinus cavity is attained by creating an access port through the tooth socket, and into the sinus.

In another embodiment, access to the target sinus cavity is attained by creating an access port through the roof of the mouth, and into the sinus.

In another embodiment, a method of treating a deviated septum includes advancing an expandable tubular element into the nasal cavity occluded by the deviated septum, and expanding the tubular device so that the septum deflected to a more normal position.

In another embodiment, a method of treating a deviated septum includes placing an expandable tubular element into each the nasal cavity in order to properly align the septum.

In another embodiment, a method of treating a perforated septum includes advancing an expandable tubular device into the nasal cavity and expanding the tubular device so that the tubular device covers the septum perforation. Another tubular device can be placed in the adjacent nasal cavity.

In another embodiment, the tubular device has side-opening that prevent the covering and blocking of sinus side-branches.

In another embodiment, the tubular device has side-opening that allows for the linking or combining of other tubular devices in order to create a pathway within the sinus structures.

In another embodiment, the tubular device has end openings that facilitate reliable linking or extension of the tubular pathway.

In another embodiment, foams or hydrogels can be injected around the tubular devices in order to help reconstruct biologic mass for the treatment of Empty Nose Syndrome.

In yet another inventive embodiment, the Bridge is positioned within the nasal cavity and used to seal the fistula-type defect seen in Cleft Palate (i.e. incomplete, unilateral or bilateral). Velopharyngeal Insufficiency can thus be treated as a direct result of this procedure. The palate can be attached or sutured to the Bridge in a modified palatoplasty oricedure to aid in further sealing the opening in the palate. In this embodiment, as well as others, a covering on the Bridge also assists in maintaining a seal as well as a structure to suture too. The tubular structure of the Bridge allows for proper airflow through the nose. The structure can be a permanent implant or appliance, temporary, or of a design which is biodegradable and/or bioabsorable.

In another embodiment, the delivery system is guide over a guidewire.

In another embodiment, the delivery system is advanced through a guide catheter.

In another embodiment, the delivery device is advanced over an endoscope.

In yet another embodiment, the guidewire is manufactured of fiber optic materials in order to allow for light transmission and optical visualization.

Further features and advantages will become apparent upon review of the following drawings and description of the preferred embodiments.

While the invention will be described in connection with the preferred embodiments, it will be understood that it is not intended to limit the invention to those embodiments.

BRIEF DESCRIPTION OF THE DRAWINGS

Throughout the several views of the drawings several illustrative embodiments of the invention are disclosed. It should be understood that various modifications of the embodiments might be made without departing from the scope of the invention.

Throughout the views identical reference numerals depict equivalent structure wherein:

FIG. 1 is a diagram showing the advancement and deployment of the BRIDGE utilizing a catheter with an expandable element FIG. 2 is a diagram showing the advancement and deployment of a self-expanding BRIDGE FIG. 3 is a diagram showing the advancement and deployment of the BRIDGE, utilizing a catheter with an expandable element, within a compressed bone segment FIGS. 9A & 9B show the placement of a braided BRIDGE FIG. 10 shows the screws or nails used in conjunction with an implanted BRIDGE FIG. 11 shows a BRIDGE used in conjunction with external supporting elements FIGS. 12A & 12B shows an implanted BRIDGE connected to an electrical generator.

FIG. 13 shows an expansion device using a rubber grommet

DETAILED DESCRIPTION

Figure 4:
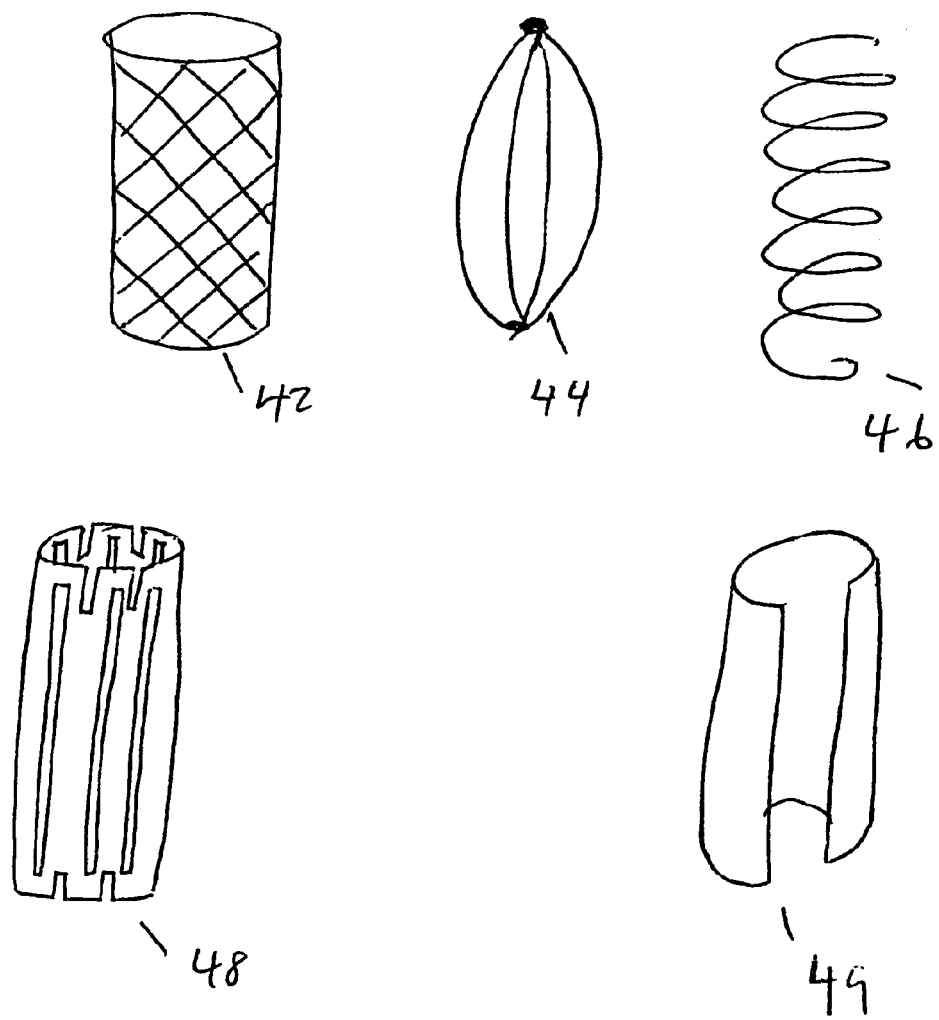
FIG. 4 shows a variety of acceptable BRIDGE structures and designs FIGS. 5A & B depict a bridge that can be expanded or contracted by relative movement of the ends of the structure

Throughout the description the term BRIDGE refers to a expandable device that is used to fixate or repair bone fractures. The device may be made of metals such as stainless steel, tantalum, titanium, Nitinol or Elgiloy and it may form an electrode for electrical stimulation. One or more electrodes may be associated with it. The BRIDGE may incorporate fiber optics for imaging, sensing, or the transmission of energy to heat, ablate, or illuminate. The device may also be made from a plastic or other non-metallic material. The BRIDGE may also incorporate a covering of polymer or other materials. The BRIDGE may also be a composition of different materials. The BRIDGE may be smooth or have cutting or abrasive surfaces. The BRIDGE can be self-expanding or use a device such as a balloon catheter to mechanically expand or further expand it. In addition, other means of expanding the BRIDGE may be utilized such as any mechanical means of expansion, or thermal, vibrational, electrical, hydraulic, pneumatic actuation. Mechanical means might employ a system consisting of a rubber grommet that expands when it is compressed axially. Another mechanical means of expansion may use a tubular array of elements such as splines, wires or braided wire that expand radially outward when compressed at each end. Another mechanical means could employ wedges in a tubular or cylindrical type of array that collectively force the BRIDGE to expand when they are moved relative to each other. The BRIDGE delivery system may also employ fiber optic technology in order to endoscopically diagnose, control placement and review procedural outcome. Likewise, a number of other technologies such as pressure monitoring, stress monitoring, volume monitoring, etc. can be employed to benefit the outcome of the procedure.

The BRIDGE may be implanted for chronic use or for acute use. In acute use, the BRIDGE is used for temporary stabilization and fixation of bone fractures. After a period of time, the BRIDGE is withdrawn.

Biodegradable materials that degrade or dissolve over time may be used to form the BRIDGE. Various coatings may be applied to the BRIDGE including, but not limited to, thrombo-resistant materials, electrically conductive, non-conductive, thermo-luminescent, heparin, radioactive, or biocompatible coatings. Materials such as calcium, minerals, or irritants can be applied to the BRIDGE in order to expedite bone growth. Drugs, chemicals, and biologics such as morphine, dopamine, aspirin, genetic materials, antibiotics and growth factors can be applied to the BRIDGE in order to facilitate treatment.

Other types of additives can be applied as required for specific treatments.

Electrically conductive BRIDGEs with electrode elements may be used with companion pulse generators to deliver stimulation energy to the bone to expedite bone growth. This electrical therapy may be used alone or in combination with other therapies to treat the affected site. Electrical therapies may be supplied from implantable devices or they may be coupled directly to external generators. Coupling between the BRIDGE and external generators can be achieved using technologies such as inductive or microwave coupling as examples. The BRIDGE may also be designed of geometries or materials that absorb radioactive energies for the treatment of bone cancer, as an example.

In the preferred embodiment, access is gained to a location on the bone that the device will pass through. A surgical incision is made through tissue to expose the entry site at the bone. The size and scope of the incision is dependent on the need for each case, Preferably, a small hole is drilled through the bone into the medullary cavity (marrow conduit). Larger holes or removal of a portion of the bone may be required dependent on the need for each case.

In the example of a fractured femur, an access location might be the either the greater trochanter or the patellar surface. In the case of a fractured humerus, the access might be made at the greater tubercle or the capitulum.

The device, on its delivery system, is then passed through the marrow cavity and positioned across the fracture.

When the right position is attained (potentially guided by CAT scan, MRI, x-ray, or fluoroscopic imaging), the fracture can be manipulated to an optimum configuration if needed, and the device is expanded or released for expansion. The delivery system is then removed after expansion.

If necessary, the access hole in the bone can be plugged with retained bone chips from the drilling procedure, fibrin or other acceptable materials.

Any surgical incision is closed with standard techniques.

It may be necessary to remove some bone marrow to facilitate placement of the BRIDGE. After placement of the BRIDGE, the marrow can be reinserted into the bone and within the BRIDGE. Another alternative treatment may be to replace the marrow with a polymeric substance that hardens after placement within the bridge and bone portions. This would enhance the immediate fixation strength. The polymeric substance can be biodegradable or otherwise metabolized by the body. In addition, the polymeric substance may incorporate drugs, antibiotics other clinically relevant substances and materials. The polymeric substance can also form a foam or cellular structure to allow for marrow formation.

Other embodiments of the BRIDGE invention can include the use of external screws that join the BRIDGE through the bone. This provides and extra measure of securement and strength.

FIG. 1A is a diagram showing the BRIDGE 10, which is mounted to a balloon catheter delivery device 11 within a segment of fractured bone 12. The entire system is advanced through an opening 13 in the bone 12. The BRIDGE 10 is positioned to span the fracture. At this point, the balloon is inflated causing the BRIDGE to expand against the inside of the bone. The balloon may be inflated via a syringe or pump 14 and a pressure gauge 15. The balloon may have a predetermined minimum or maximum diameter. In addition, the balloon can have a complex shape to provide proper placement and conformance of the device based on anatomical requirements and location. One or more inflations may be used to insure proper positioning and results. FIG. 1B shows the expanded BRIDGE 10 spanning the fracture and connecting the bone segments. The delivery device 11 is being withdrawn. If required, the balloon may be reinserted and reinflated for additional BRIDGE manipulation.

FIG. 2A is a diagram showing a self-expanding BRIDGE 20, which is compressed and inserted within a catheter delivery device 21, within a segment of fractured bone 22. The entire system is advanced through an opening 23 in the bone 22. The BRIDGE 20 is positioned to span the fracture.

At this point, the BRIDGE 20 is released from the catheter and self-expands against the inside of the bone. The release mechanism can be simply pushing the BRIDGE out of a catheter lumen or retracting a retaining sleeve. The BRIDGE self-expands due to the spring forces inherent in its materials and design. Likewise, the BRIDGE can be made of a shape-memory material such as Nitinol so that when subjected to body temperature the structure expands. With shape memory materials, the shape of the expanded device can be predetermined. Additionally, the device can be retrieved, repositioned, or removed by using temperature-based shape-memory characteristics.

FIG. 2B shows the expanded BRIDGE 20 spanning the fracture and connecting the bone segments. The delivery catheter 21 is being withdrawn.

In the self-expanding case, the tubular mesh has a predetermined maximum expandable diameter.

FIG. 3A shows a BRIDGE 30 on a balloon catheter 31 being advanced into a crushed area of a bone.

FIG. 3B shows the BRIDGE 30 expanded within the crush zone causing the crushed bone to resume its original diameter. The same results can be attained using any of the aforementioned BRIDGE designs, such as self-expanding or manually expanded, and placement methods. In the case of self-expanding designs, further expansion of the BRIDGE can be performed using a balloon catheter or another type of expansion device such as those mentioned within this invention or can use solid dilator rods.

FIG. 4 shows a variety of possible BRIDGE shapes and geometries. A tubular mesh 42, a multi-element spline 44, a coil 46, slotted tube 48, and a clam-shell or sleeve 49. In the case of slotted tube, other geometric configurations of the slots (i.e.; hexagonal, sinusoidal, circular, meandering, spiraling, and multigeometric patterns) may be utilized alone or in conjunction with a combination thereof. Likewise, variations in the geometry of any of the BRIDGEs may be altered to achieve desired performance criteria such as radial strength, longitudinal flexibility or stiffness, expansion ease, profile, surface area, mass and volume, and material selection. The elements of the BRIDGE may be porous, have through holes, or have a covering. In addition, the surface of the bridge may be textured, rough, and sharp or have cleats or small pins integrated or attached. Each of the various shapes and geometries may find its own specialized use in the treatment of specific type of bone fractures.

Figure 5:
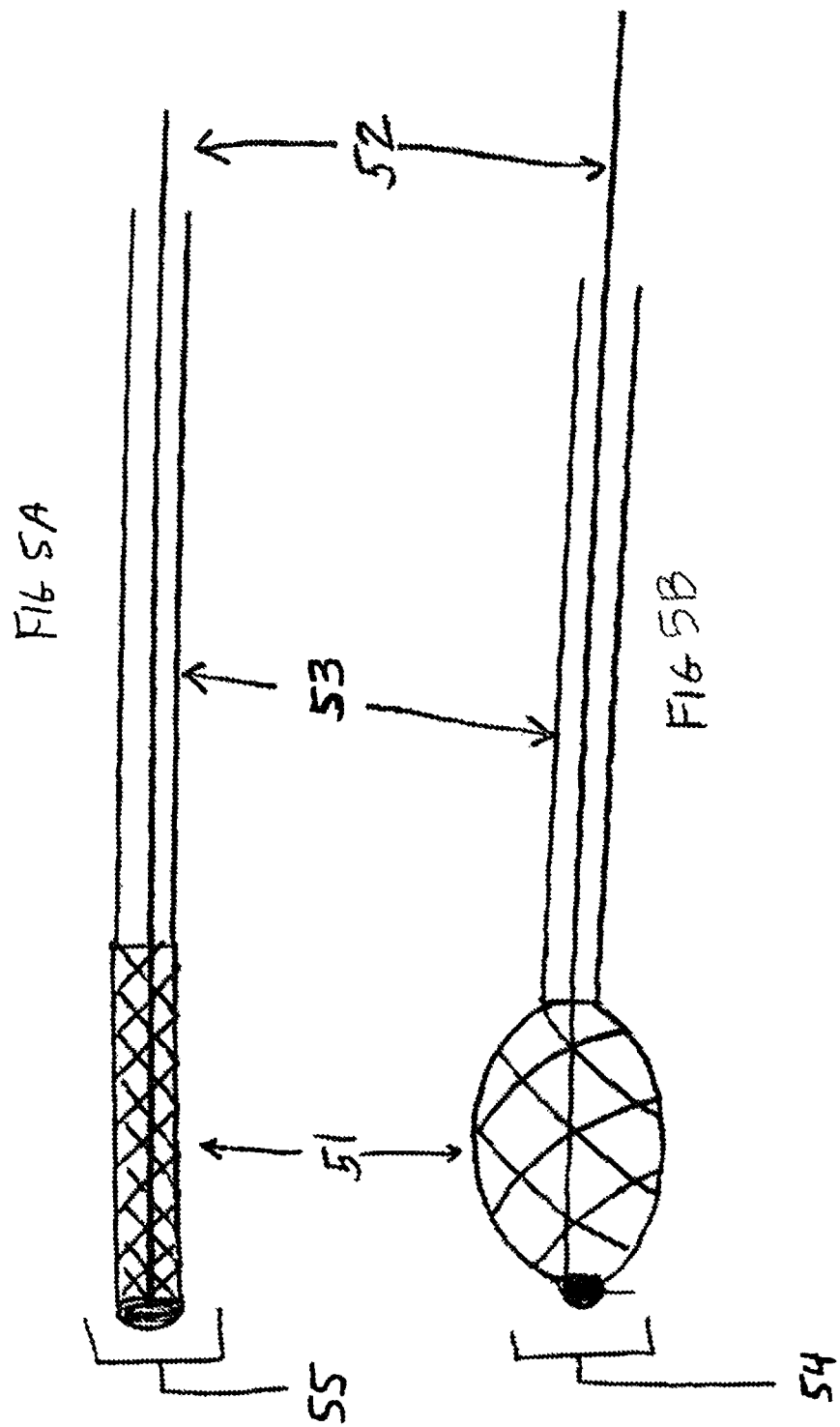

FIG. 5 shows two states of a manually expandable BRIDGE device 51. The device consists of a coaxial shaft 52 and tube 53 arrangement. Attached to the distal end of the shaft 52 and the tube 53 is a braided mesh tube BRIDGE 51. When the shaft 52 and tube 53 are moved opposite of the other by manipulating the proximal ends, the BRIDGE 51 expands 54 or contracts 55. In this case, the BRIDGE 51 can be made of any structure that expands and contracts such as a coil, splined-elements, etc. The various methods of expanding and contracting these structures are, but not limited to, push-pull, rotation, and balloon manipulation. In this type of device, direct connection to either an electrical generator, laser, or monitoring system can be made. In addition, it be envisioned that a device of similar nature be connected to a mechanical energy source, such as rotational or vibrational sources.

Figure 6:
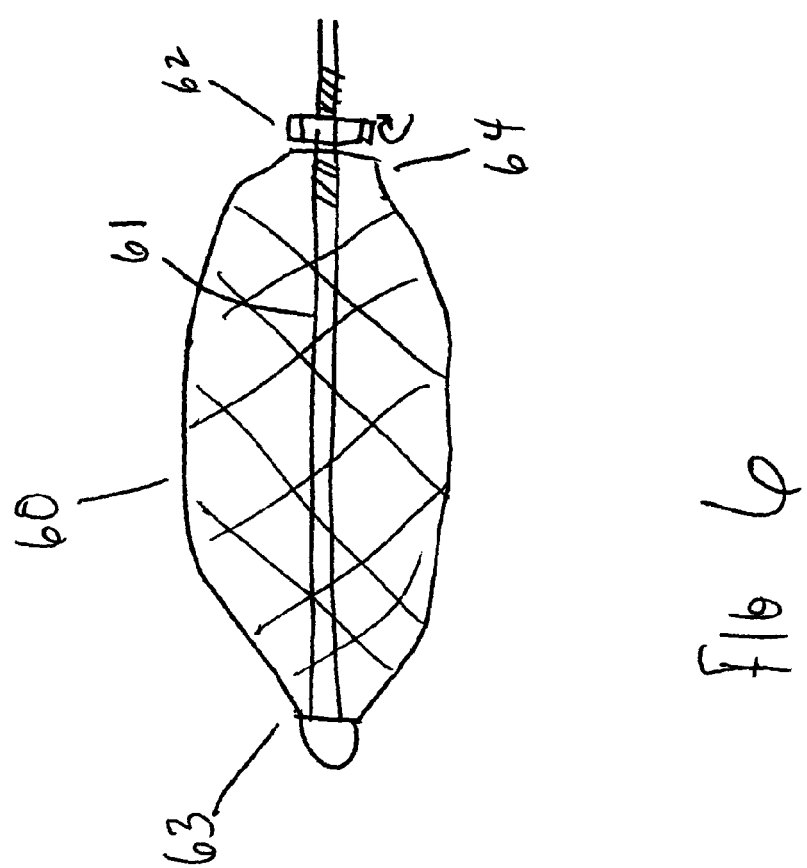
FIG. 6 shows a bridge that can be expanded or contracted by relative movement of the ends of the structure

FIG. 6 shows a manually expanded BRIDGE 60 with an internal rod 61 and compression nut mechanism 62. One end of the BRIDGE is fixed to one end of the rod 63, while the other end 64 is allowed to move relative to the rod. As the compression nut is tightened, it forces the end 64 of the BRIDGE to move, thus compressing the BRIDGE and forcing it to expand. Using a customized tool, the compression nut is tightened and the BRIDGE expanded until the desired affect is achieved. The nut can have a locking mechanism, such as a lock washer or other means, to maintain position. Alternatively, the nut and rod components can be exchanged for a bolt and nut or a bolt and internally threaded tubular rod. In any event, the expansion is caused by the relative movement of a a screw threaded mechanism.

Figure 7:
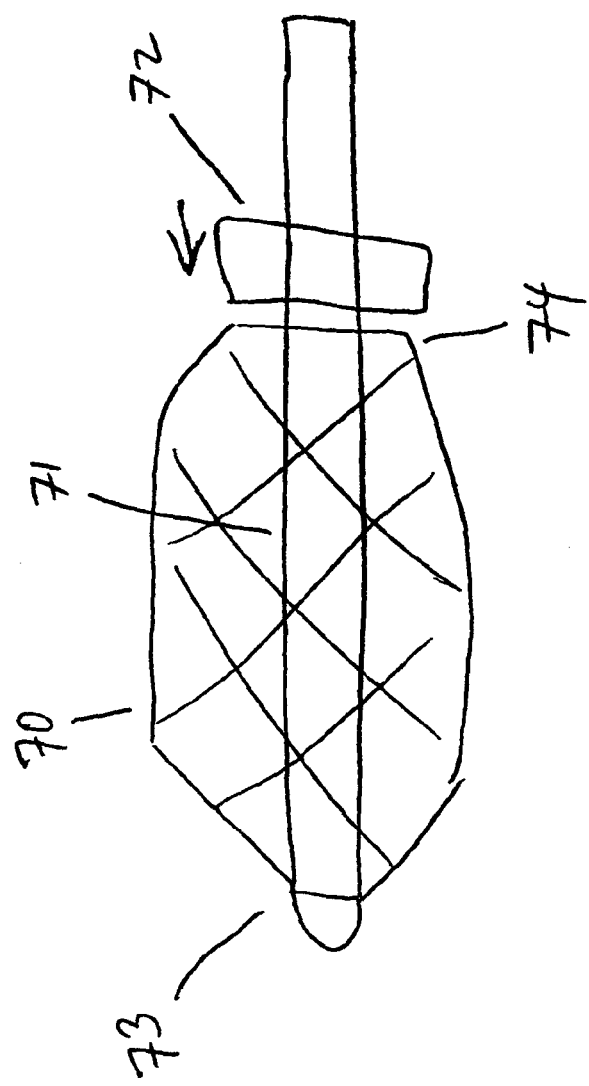
FIG. 7 shows a bridge that can be expanded or contracted by relative movement of the ends of the structure

FIG. 7 shows another manually expanded BRIDGE 70 with an internal rod 71 and compression element 72. One end of the BRIDGE is fixed to one end of the rod 73, while the other end 74 is allowed to move relative to the rod. As the compression element is pushed forward, it forces the end 74 of the BRIDGE to move, thus compressing the BRIDGE and forcing it to expand. The compression element is advanced and the BRIDGE expanded until the desired affect is achieved. The element can maintain its position utilizing mechanical friction or a detent mechanism. Other means of maintaining position are possible. The internal rod of the manually expanded BRIDGEs may be flexile or rigid. The expanding elements of the manually expanded BRIDGEs may utilize geometries such as those discussed in FIG. 4

Figure 8A:
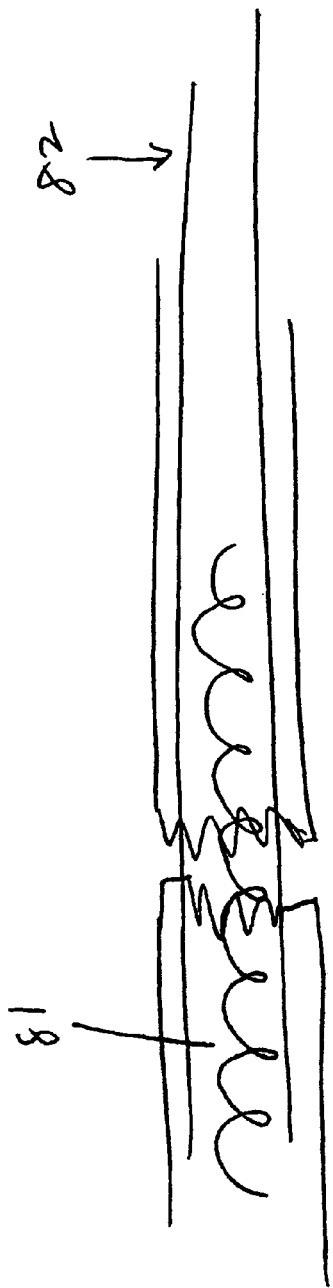
FIGS. 8A & 8B show the placement of a coil BRIDGE
Figure 8B:
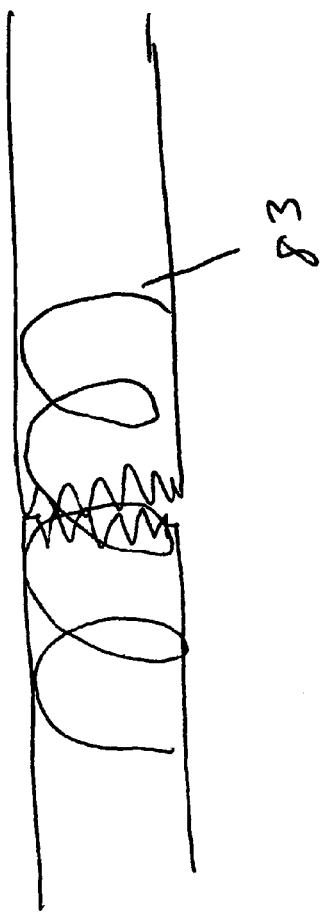

FIGS. 8A & 8B show the use of a coil BRIDGE. The coil BRIDGE 81 is advanced to the fracture in a stretched state with a diameter less than its natural, unstretched diameter. When it is released from the delivery device 82, the coil BRIDGE expands to a state of greater diameter. As it expands to a greater diameter 83 it naturally shortens in length. This simultaneously draws the fracture together and fixates the fracture.

FIGS. 9A & 9B show the use of a braid BRIDGE. The braid BRIDGE 91 is advanced to the fracture in a stretched state with a diameter less than its natural, unstretched diameter. When it is released from the delivery device 92, the braid BRIDGE 93 expands to a state of greater diameter. As it expands to a greater diameter it naturally shortens in length. This simultaneously draws the fracture together and fixates the fracture. The devices in FIG. 8 and FIG. 9 can utilize other geometries that function similarly with similar results. In addition, shape memory materials that exhibit similar change of length and diameter may be used in the construction of devices in FIG. 8 and FIG. 9.

FIG. 10 shows the BRIDGE 100 invention including the use of external screws 101 that join the BRIDGE through the bone. This provides an extra measure of securement and strength.

FIG. 11 shows external plates 10 incorporated with this combination of external screws 111 and BRIDGE 112. There maybe fractures that require the additional stabilization that this combination provides.

FIG. 12A shows an implanted bridge 120 connected to an electrical generator 121 in order to expedite bone growth. The external screws in FIG. 10 can serve the dual purpose of adding securement and acting as, electrodes 122.

FIG. 12B shows a device 123 similar to that in FIG. 5 that is connected to an electrical generator 124. In this scenario, the BRIDGE can be used is in a temporary or permanent fashion. It may be desirable to remove the BRIDGE after the bone has healed.

FIG. 13 shows a expansion device 130 that uses a rubber sleeve or grommet 131 that when compressed axially 132, expands radially 133.

It should be apparent that various modifications might be made to the devices and methods by one of ordinary skill in the art, without departing from the scope or spirit of the invention.

These devices and methods which have been discussed in the preceding detailed description are also suitable for treating afflictions of various cavities and orifices such as the nasal sinus cavity. The afflications include, but are not limited to, deviated septums, broken nose, damaged sinus structures, bloody nose, sinusitis, perforated septums, sinus fistula, deft palates and sinus cancer.

Figure 14:
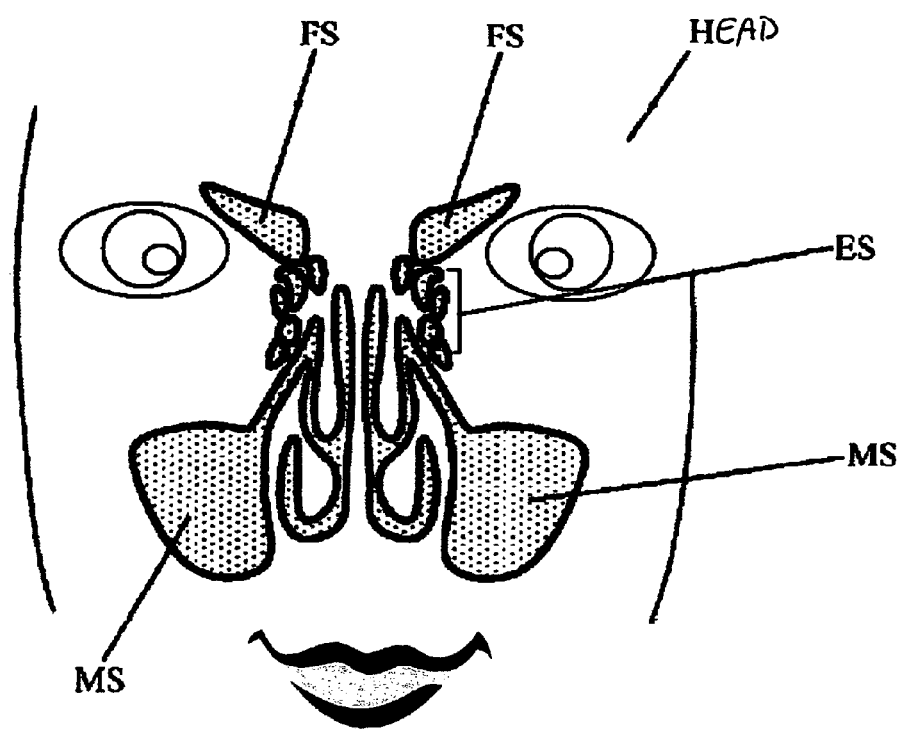
FIG. 14. is a diagram of a patients head showing the major sinus cavities

FIG. 14 shows three of the four major nasal sinus cavities:
the maxillary sinuses (MF), also called the maxillary antra and the largest of the paranasal sinuses, are under the eyes, in the maxillary bones (cheek bones).
the frontal sinuses (FS), over the eyes, in the frontal bone, which forms the hard part of the forehead.
the ethmoid sinuses (ES), which are formed from several discrete air cells within the ethmoid bone between the nose and the eyes.
the sphenoid sinuses, in the sphenoid bone at the center of the skull base under the pituitary gland.

Figure 15:
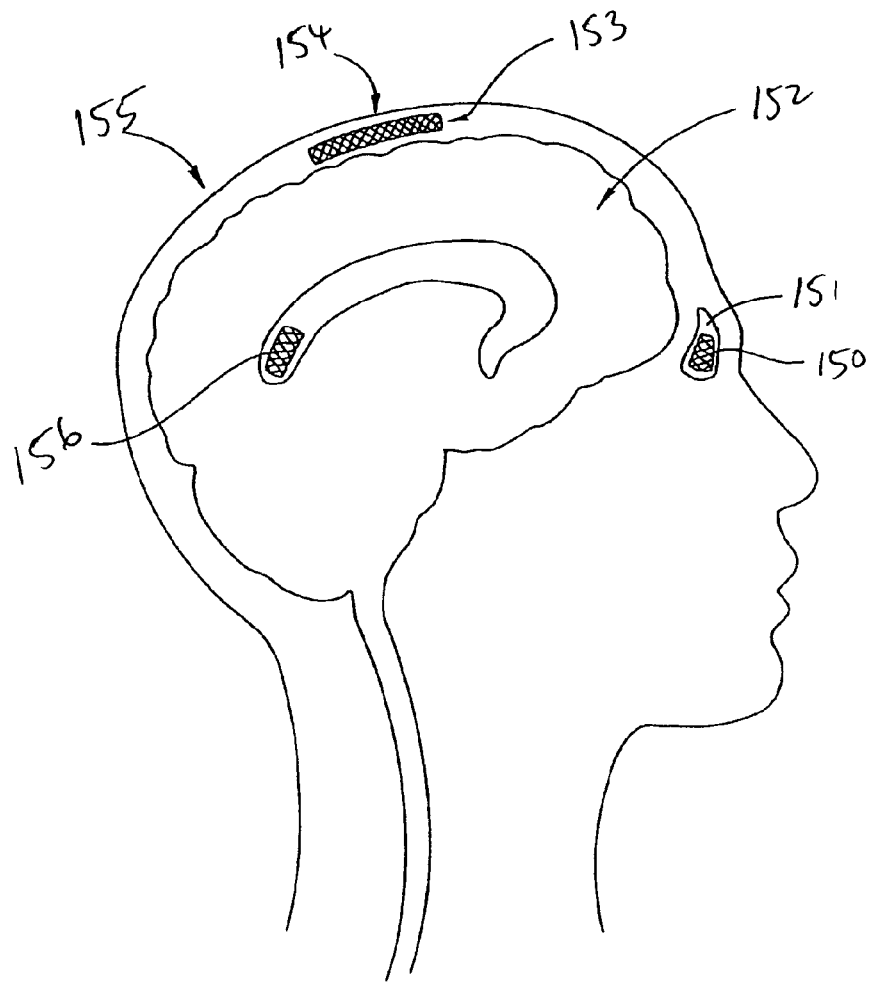
FIG. 15 is a diagram of the head showing a Bridge located in the frontal sinus cavity and other locations.

FIG. 15 shows an expandable device 150 similar to the Bridge positioned within the frontal sinus 151. FIG. 15 is taken from the incorporated references by Mische (i.e. U.S. Pat. No. 6,375,666 filed Dec. 9, 1999 entitled "Methods and Devices for the Treatment of Neurological Disorders") and identified as FIG. 2 in these references for treating neurologic disorders and physiologic disorders. However, one skilled in the art can appreciate the obviousness and inventiveness provided by the figure in depicting the ability of the expandable device for maintaining patency of the sinus cavity, specifically the frontal sinus cavity.

Figure 16A:
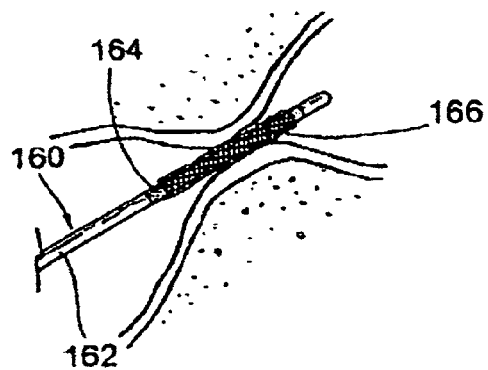
FIG. 16A, 16B, 16C depicts a sequence of Bridge placement in the sinus cavity.
Figure 16B:
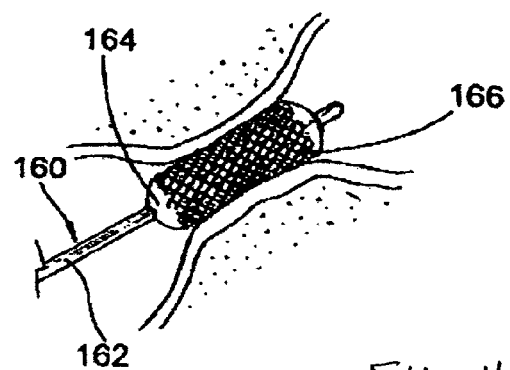
Figure 16C:
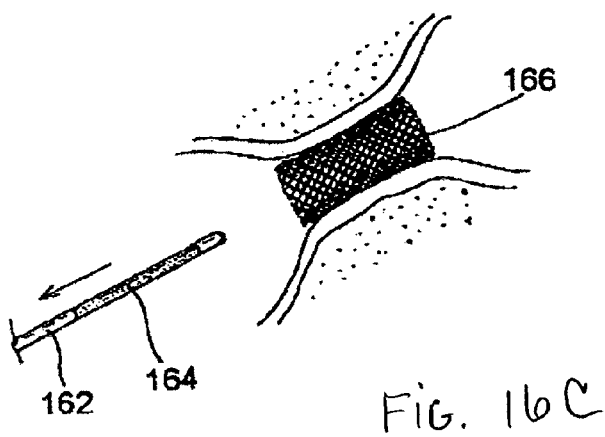

FIG. 16A, FIG. 16B and FIG. 16C shows a sequence of the placement of the Bridge within the sinus. These figures are similar to the FIGS. 3A and 3B which show a bone structure being dilated and are in the pending U.S. patent application having Ser. No. 09/733,775 filed on Dec. 8, 2000 entitled "Methods and Devices for Treatment of Bone Fractures", of which this application claims the benefit of. U.S. patent application having Ser. No. 09/733,775 discusses treating the sinuses and nose with the Bridge and associated technology.

The figures show a device 160 and method for delivery of a expandable Bridge 166. This device 160 comprises a flexible catheter 162 having a balloon 164 thereon. Initially, as shown in FIG. 16A, the balloon 164 is deflated and the Bridge 166 is radially compressed to a collapsed configuration, around the deflated balloon 164. The catheter 162 with the balloon 164 deflated and the collapsed Bridge 166 mounted thereon is advanced into a passageway such as a nostril, nasal cavity, meatus, ostium, interior of a sinus, etc. that is to be expanded or dilated by Bridged. Thereafter, the balloon 164 is inflated causing the Bridge 166 to expand to a size that frictionally engages the surrounding tissue so as to hold the Bridge 166 in place, as shown in FIG. 16B. In some instances the procedure will be performed for the purpose of enlarging a passageway (e.g., an ostium, meatus, etc.) and the Bridge 166 will be expanded to a diameter that is sufficiently large to cause the desired enlargement of the passageway and the Bridge will then perform a scaffolding function, maintaining the passageway in such enlarged condition. After the Bridge 166 has been fully expanded and implanted, the balloon 164 may be deflated and the catheter 162 removed as shown in FIG. 16C. In some applications, the Bridge may contain a diagnostic or therapeutic substance as defined herein and such substance may elute from the Bridge 166 into the surrounding tissue to bring about a desired diagnostic or therapeutic effect. In some cases, the Bridge 166 may be permanently implanted. In other cases the Bridge 166 may be temporarily implanted. In cases where the Bridge 166 is temporarily implanted, it may be removed in a second procedure conducted to retrieve the Bridge 166 or the Bridge 166 may be made of bioabsorbable or biodegradable material such that it degrades or is absorbed within a desired period of time after implantation. In some cases, such as when the Bridge is to be placed within the ostium of a paranasal sinus, the Bridge and/or the balloon may be specifically shaped to facilitate and/or cause the Bridge 166 to form and seat in a desired position and to prevent unwanted slippage of the Bridge 166. For example, the Bridge 166 and/or balloon 164 may have an annular groove formed about the middle thereof or may be hourglass or venturi shaped, to facilitate seating of the Bridge 166 within an ostium or orifice without longitudinal slippage of the Bridge 166. In some cases it may be desirable to leave a tether or suture attached to the Bridge 166 to allow for simple removal of the Bridge 166. In some cases the procedure may be intended to mechanically remodel or enlarge a sinus location. In this case, the dilating force of the delivery device (e.g. balloon, grommet, expansion tool, etc) is strong enough to cause bone or cartilage to yield, deform or break. Assisting in this phenomena would be a Bridge such as that shown in FIG. 19A and FIG. 19B where physical features on the exterior of the Bridge facilitates cutting or breaking of the sinus structure. This will be further elaborated in the upcoming description of FIGS. 19A and 19B.

Figure 17A:
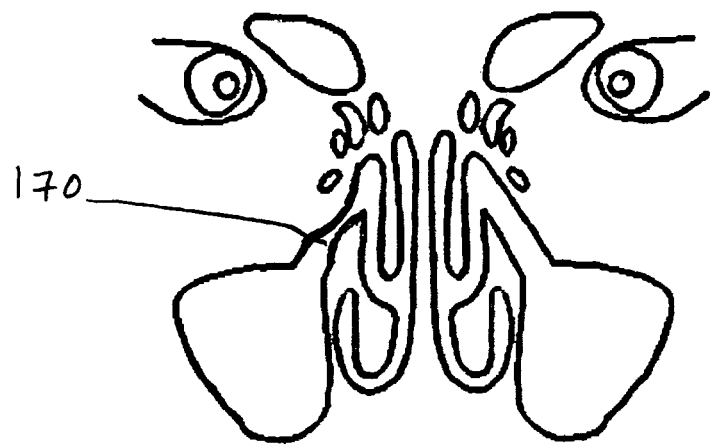
FIGS. 17A & 17B shows a sinus before and after a Bridge placement.
Figure 17B:
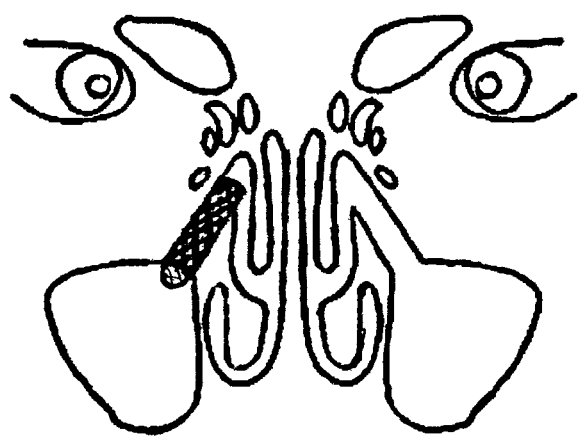

FIG. 17A shows a constricted sinus passageway 170. The constriction could be the result of sinusitis-related inflammation, trauma, lesion, polyp, tumor, or other condition. FIG. 17B shows a tubular Bridge that has been placed at the constriction and thus resulting in an increase of the passageway opening. A Bridge of similar designs and method of placement may be used in the nasopharynx to maintain patency for fluid drainage as well as to treat sleep apnea. In sleep apnea, many times the nasopharynx will be occluded or collapse during the sleep cycle. When it collapses, a natural respiratory pressure release via the nasal passage is blocked and a vacuum is formed in the back of the mouth and the throat. This phenomenon exacerbates the soft palate prolapse into the throat and causes sleep apnea. Using a Bridge within the nasopharynx will ensure air passage through the nose, and prevent nasopharynx collapse and avoid the vacuum formed when this happen. The soft palate can be attached to the Bridge residing in the nasopharynx in order to maintain the position and shape of the soft palate. This will prevent the soft palate from prolapsing into the throat and blocking breathing. The attachment means can be sutures, clips, staples, pins, screws, nails, or other means of attachment.

Although the Bridge can be delivered via the nasal passage, as illustrated in FIGS. 1 and 2, access to the sinus cavity can be gained through an access hole made in the bone structures of the face. Such bone structure can be the maxilla, uncinate process of ethmoid bone, or more specifically the canine fossa. One option for accessing the sinus cavity is to dissect the tissue above the top gum line, exposing the bone structure. A hole can then be made in the bone structure by drill, punch, probe, scalpel, cannula as examples. With the hole into the sinus cavity created, the Bridge can then be advanced to the sinus cavity treatment site. Another option is to drive an introducer cannula simultaneously through the gum tissue and the bone structure. The cannula can have an inner coaxial element with a sharp tip that extends past the tip of the cannula. This arrangement aids in driving the cannula through the tissue and bone structure, as well as preventing the cannula from getting clogged with tissue and bone. The inner coaxial element is then removed allowing for passage of devices (i.e. Bridge and delivery system) through the cannula and into the sinus cavity.

Figure 18A:
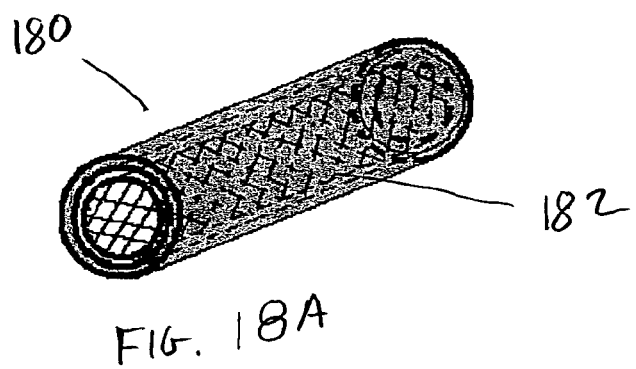
FIGS. 18A, 18B, and 18C show a covered expandable Bridge device in various states of expansion.
Figure 18B:
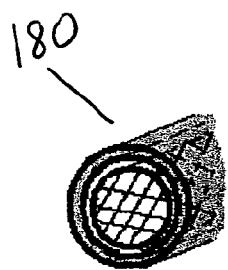
Figure 18C:
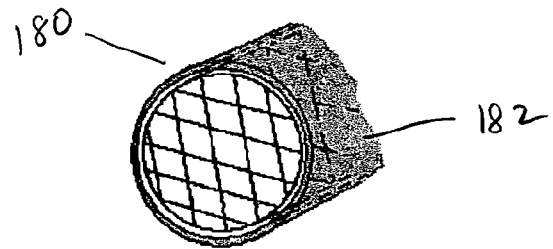

FIGS. 18A, 18B, and 18C show a Bridge 180 with an exterior coating 182 in various views. FIG. 18A shows the entire Bridge 180 device in a pre-expanded state. FIG. 18B shows a section of the Bridge 180 in a pre-expanded state and its exterior coating 182 intact. FIG. 18C shows a section of the Bridge in the post-expanded state. The exterior coating can be made of a fabric material that aids in compressing the lining of the sinus in order to expedite hemostasis of a bloody nose. The BRIDGE can coatings such as drugs, minerals, gauze, fabric, lubricants or other materials that assist in causing hemostasis. A tubular form would allow air passage through the BRIDGE and maintain patient comfort; however other forms can are anticipated. As mentioned in the parent case, U.S. patent application having Ser. No. 09/733,775 filed on Dec. 8, 2000 entitled "Methods and Devices for Treatment of Bone Fractures", the BRIDGE can also be connected to an RF generator to assist in healing, as well as creating coagulation and hemostasis. In addition, the Bridge and/or the coating can be loaded with therapeutic substances such as antibiotics like used are amoxicillin (Amoxil, Larotid, Trimox), cefaclor (Cedor), and telithromycin (Ketek). Or decongestants reduce the swelling of the mucous membranes in the nose. Some examples may include oxymetazoline hydrochloride (Afrin) and phenylephrine hydrochloride (Neo-Synephrine, Sinex Decongestant Nasal Spray). Analgesics, such as aspirin, acetaminophen or ibuprofen, can be added to relieve pain. Corticosteroids, such as beclomethasone dipropionate (Beconase, Vancenase) or prednisone (Deltasone, Prednicen-M), to reduce inflammation in the nasal passages and may be given as an inhaled nasal spray that is absorbed by the Bridge and/or Bridge coating. Mucolytics, such as guaifenesin (Robitussin), can be used to thin the mucus. These medications can be added or incorporated into the Sinus Bridge in order to provide acute or sustained localized complementary treatments that persist over a time that is equivalent to that of oral medications. In a tubular form of the Sinus Bridge, air flow through the device allows for patient comfort and, thus, improved treatment compliance and treatment success is anticipated. Inhaled antibiotics are a fairly new treatment choice for chronic sinusitis. Initial studies show that because inhaled antibiotics make direct contact with the mucous membranes, they may be effective when other treatments have failed. The Sinus Bridge may have materials which absorb these inhaled antibiotics or other medications which are introduced through the nose. When absorbed by the Sinus Bridge, the localized and sustained direct affects that persist for a prescribed period of time. The absorbent materials can consist of, but not limited to, fibrous, expanded PTFE, chemicals, compounds, gels, foams, liquids, and porous materials.

Radioactive substances can also be incorporated into the Bridge and/or Bridge coating so as to treat ailments such as aggressive infections or cancer. Obviously, other medicates or therapeutic substances can be incorporated as required.

The coating can also absorb therapeutic or diagnostic substances when mist, fluids, sprays, vapors or fumes are inhaled. This allows for localized treatment of sinus ailments. The coating 182 may also be a material that is biodegradable or bioabsorable at a rate that is prescriptive.

Figure 19A:
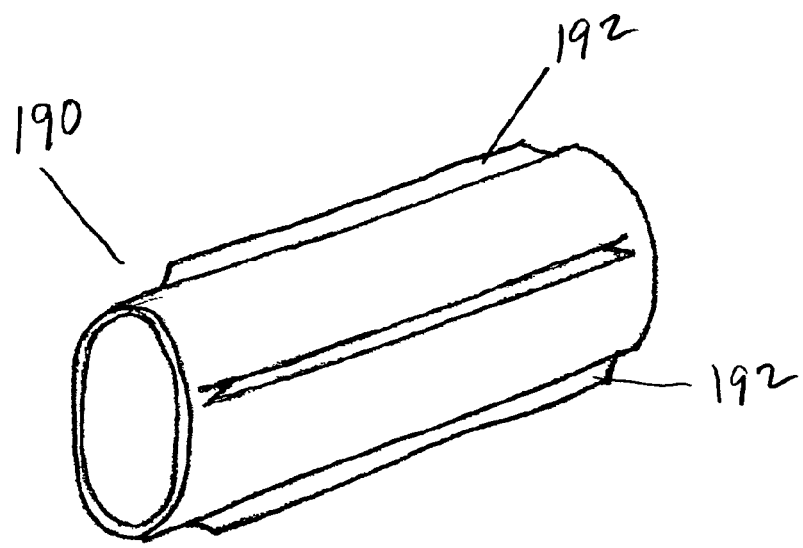
FIGS. 19A & 19B shows views of a Bridge tubular element with cutting elements on its external surface.
Figure 19B:
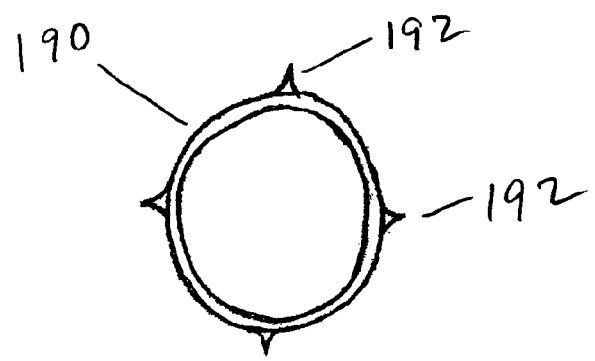

FIGS. 19A and 19B are views of a Bridge 190 that has four cutting elements 192 on the exterior surface. The number and orientation of the cutting elements 192 can be varied. For example, the cutting elements can spiral around the Bridge surface or be interrupted in a predetermined pattern. The cutting elements 192 provide the ability to cut into tenacious tissue or bone structure. In this embodiment, dilation of the tissue is eased and scar formation and be predetermined. In addition, the cutting elements embed into the biologic tissues resulting in increased fixation of the Bridge.

Figure 20A:
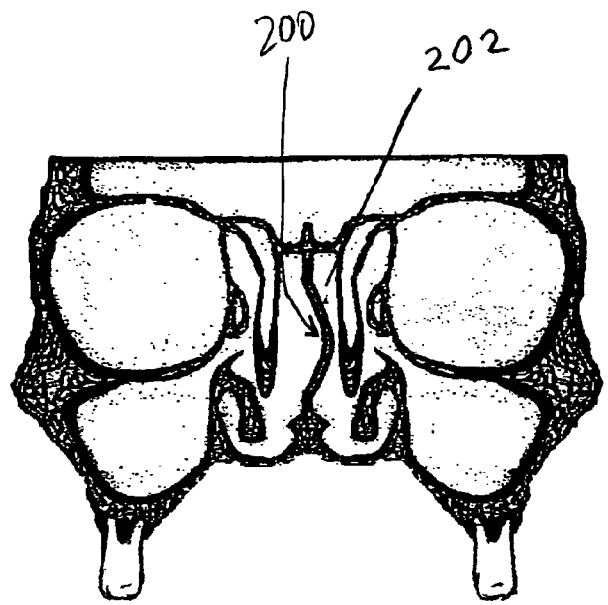
FIGS. 20A & 20B are schematic diagrams of the Bridge correcting and supporting a deviated septum.
Figure 20B:
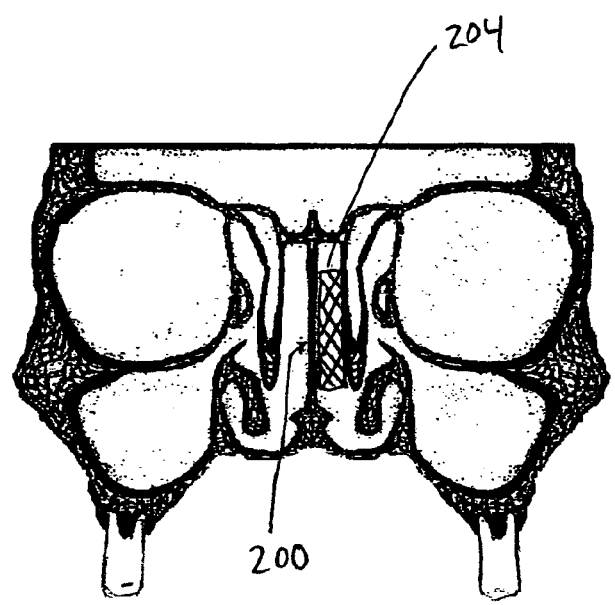

FIG. 20A shows a deviated septum 200 that is occluding the nasal passage 202. FIG. 20B shows an implanted tubular Bridge 204 that has pushed the deviated septum 200 back into proper alignment. The tubular Bridge allows for air passage through its interior lumen. The Bridge may also be used to force apposition of polyps or other occlusive anatomy against the walls of the passageways and out of the passageways to allow for proper air flow and fluid flows.

Figure 21A:
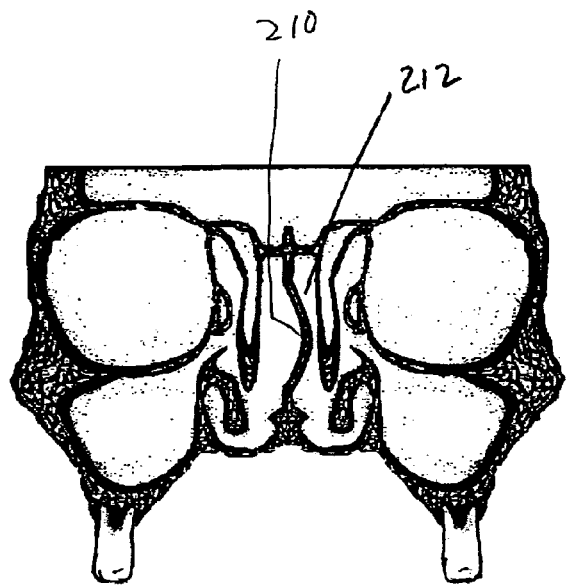
FIGS. 21A & 21B are schematic diagrams of bilateral Bridges correcting and supporting a deviated septum.

FIG. 21A shows a deviated septum 210 that is occluding the nasal passage 212. A first Bridge 214 is placed into the nasal passage 212 and pushes the deviated septum back into proper alignment. A second Bridge 216 is placed into the adjacent nasal passage 218. Alternating the sequence can be done in order to get the best outcome. The Bridge can be delivered on a balloon-delivery device and then expanded. Alternatively, the Bridge can be a self-expanding design that is positioned in place, allowed to expand, and forces the deviated septum to change alignment. If necessary, the self-expanding Bridge can be further expanded by an expansion element (e.g. balloon, grommet, wedge, tapered mandrel, etc). In this type of treatment, it may be beneficial to utilize one or more Bridges that are made of magnets or magnetic materials. Both Bridges may have magnet properties that result on the adjacent Bridges in each nasal passage to be magnetically coupled and maintain there position as well as exert force on the deviated septum keeping it in proper alignment. Alternatively, one Bridge could be composed of magnet materials while the other would be made of magnetic materials that are attracted to the adjacent magnet Bridge. If preferred, the Bridges may be joined through the septum by sutures, clips, staples, tacks, nails or other means. In all variations, the material can be partially or entirely made of materials that biodegrade and/or are bioabsorable.

Figure 21B:
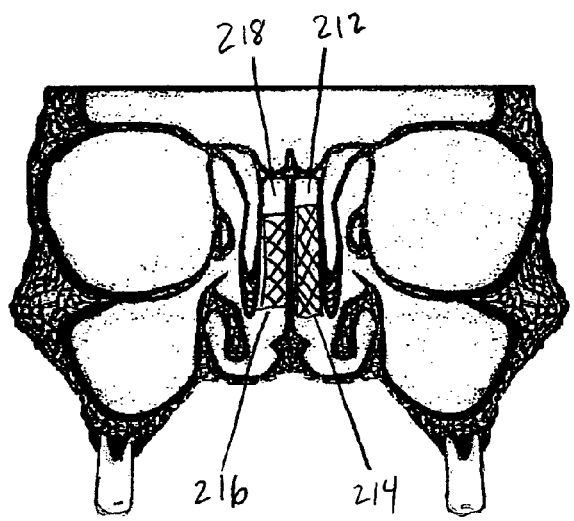
Figure 22A:
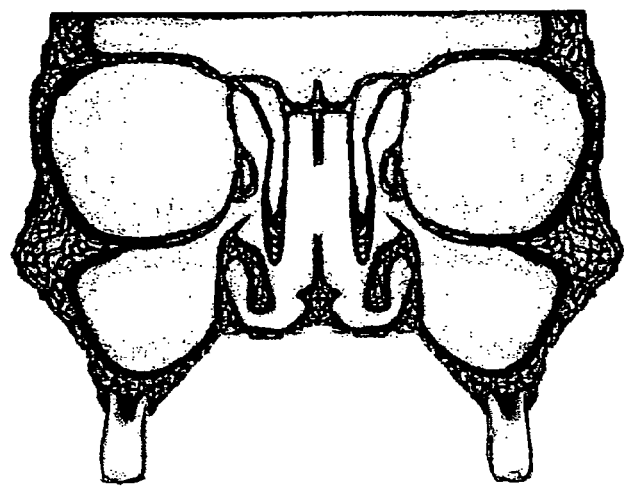
FIGS. 22A & 22B are schematic diagrams of a Bridge correcting a perforated septum.
Figure 22B:
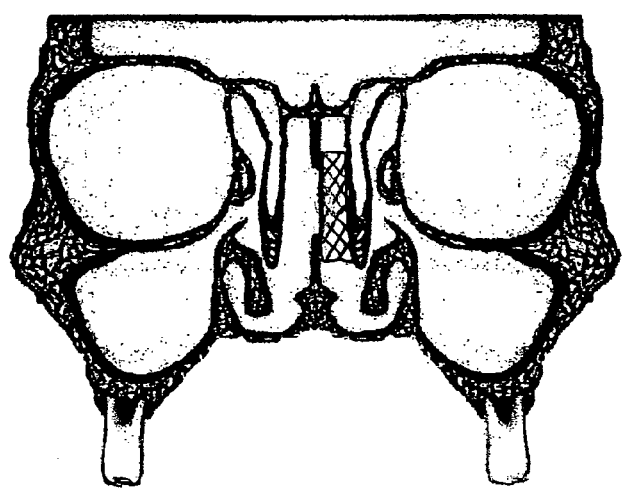

FIG. 22A shows a septum with a perforation. FIG. 22B shows a Bridge in one nasal passage. The Bridge is covering the perforation, thus isolating one nasal passage from the other. The Bridge may have a coating or covering on the external surface. This coating or covering can be a tissue or fabric, Such as in FIG. 21B, bilateral Bridges can be used if so needed. Likewise, the Bridge may be made of magnet or magnetic materials, and can be joined through the septum if so desired.

Figure 23A:
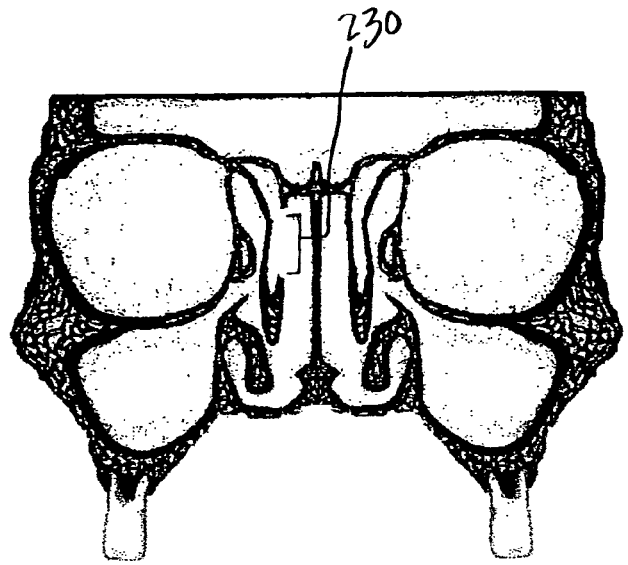
FIGS. 23A & 23B are schematic diagrams of the Bridge sealing a fistula connecting 2 sinus cavities.
Figure 23B:
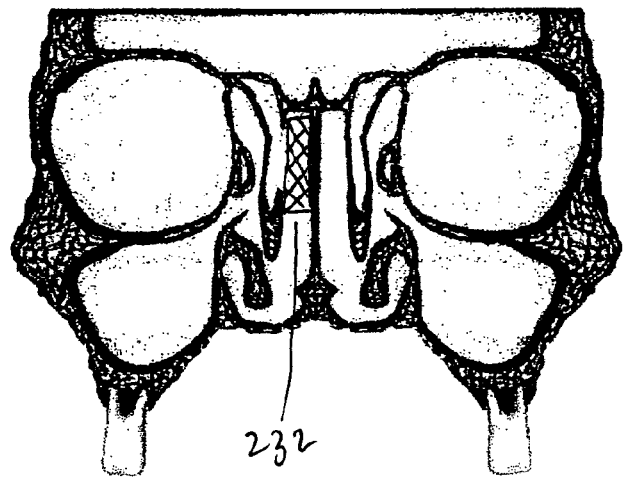

FIG. 23A shows a fistula 230 from one sinus passage into another. This can be treated with the Bridge 232 in one or more variations as discussed in FIGS. 21A through 22B. The same type of Bridge device can be used to seal a fistula between the sinus and brain cavities.

Figure 24A:
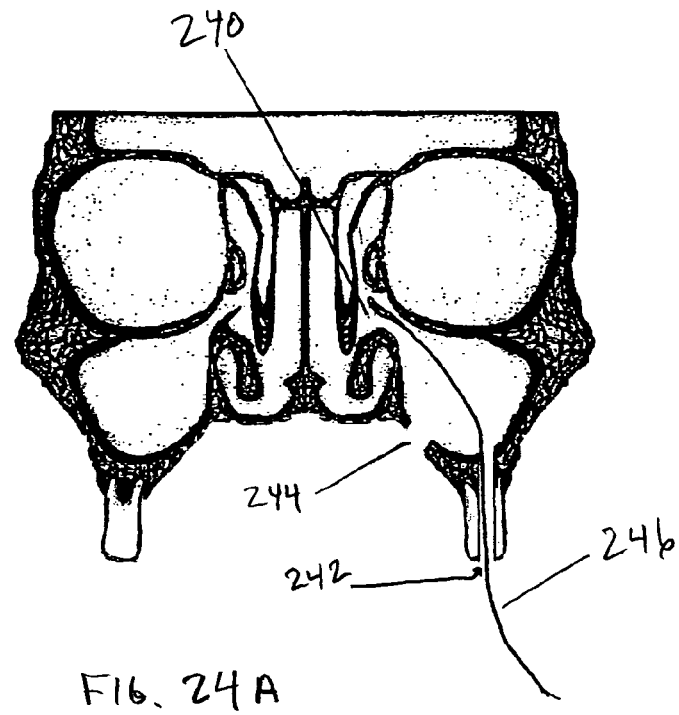
FIGS. 24A & 24B are schematic diagrams of showing steps in a procedure for placing a Bridge in the sinus cavity by advancing through the tooth and tooth socket.
Figure 24B:
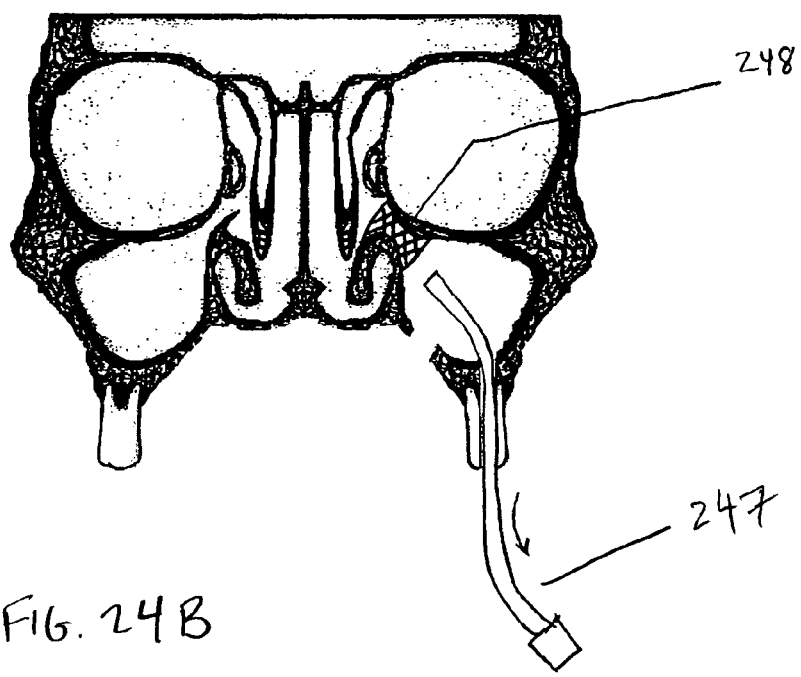

FIGS. 24A and 24B show devices in the sequence of treating a sinus passageway by gaining access through the tooth 242 and tooth socket. Alternatively, the sinus can be access through the roof of the mouth by gaining access through a hole 244 in the bone structure of the oral cavity. A device similar to a guidewire 246 is advanced through the tooth and across the sinus location to be treated. A delivery device 247 is then advanced to the sinus treatment location and the Bridge 248 is deployed. The delivery device 247 is then retracted. The hole in the tooth can be dosed with standard dental materials. Another entry point into the sinuses could be the tear ducts. In fact, these Bridge technology can be use to support the tear duct in order to maintain proper drainage of tear fluids. As well, the Bridge can be placed across the ear drum in order to release pressure and fluid build up. In this case, the Bridge would again be placed in a low profile fashion through and placed across the ear drum and expanded. It would then be left in place to allow drainage through the lumen. It could then be removed as in the previously mentioned methods. The benefit of this over a standard drain plug is that expanding slowing to a larger diameter may be safer and allow for a less traumatic affect to the ear drum.

Figure 25A:
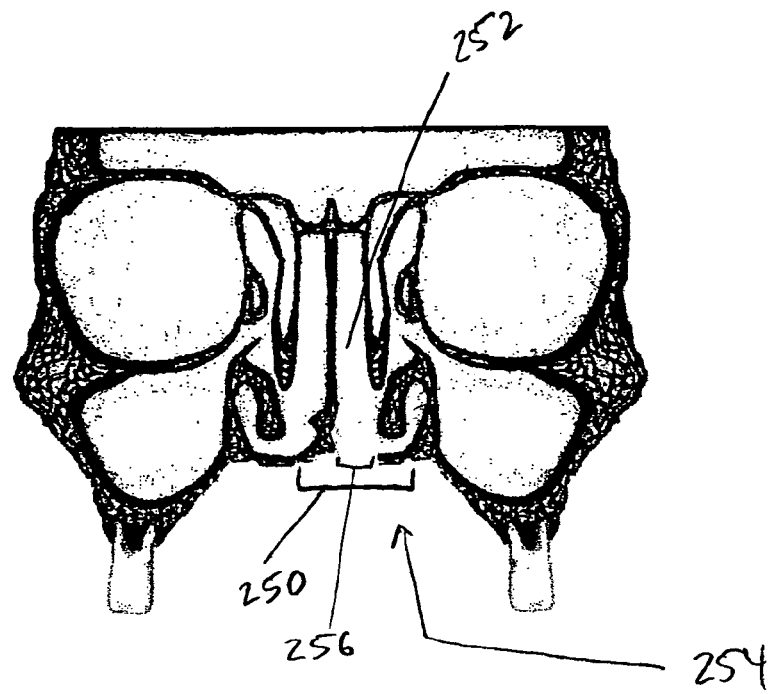
FIGS. 25A & 25B are diagrams that show the Bridge treating a unilateral cleft palate
Figure 25B:
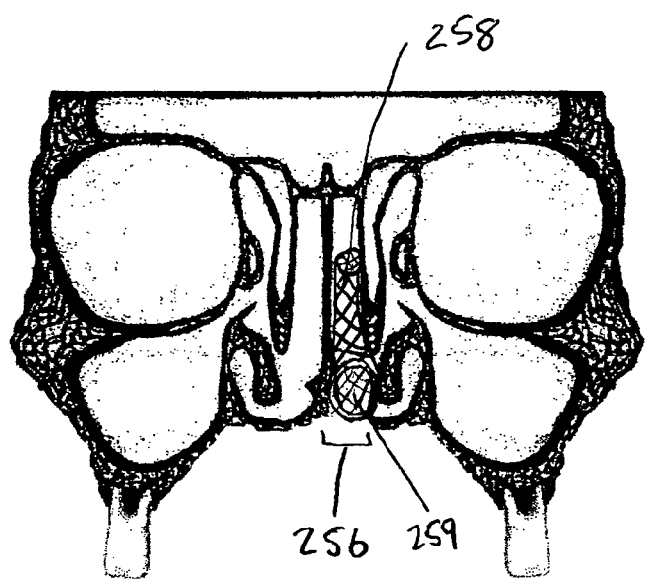

FIG. 25A shows a unilateral cleft palate 250. The nasal passage 252 and the oral cavity 254 are now in direct communication via a fistula 256 that is formed by the deft palate 250. The fistula 256 is sealed by placing a tubular Bridge 258 into the nasal passage. A covering on the Bridge, similar to that discussed in FIG. 18A would provide a barrier to fluids and air from being transferred to or from the nasal passage into the oral cavity. The axial through-lumen 259 of the Bridge allows for proper air exchange through the nose. After placement of the Bridge, the hard and/or soft palate can be attached to the Bridge if desired. The attachment means can be sutures, dips, staples, tacks, nails or other means. In all variations, the material can be partially or entirely made of materials that biodegrade and/or are bioabsorable. In addition, materials can be introduced into the space between the Bridge and the oral cavity in order to fill the void. An example would be a collagen matrix or a paste that is injected into that space.

Figure 26A:
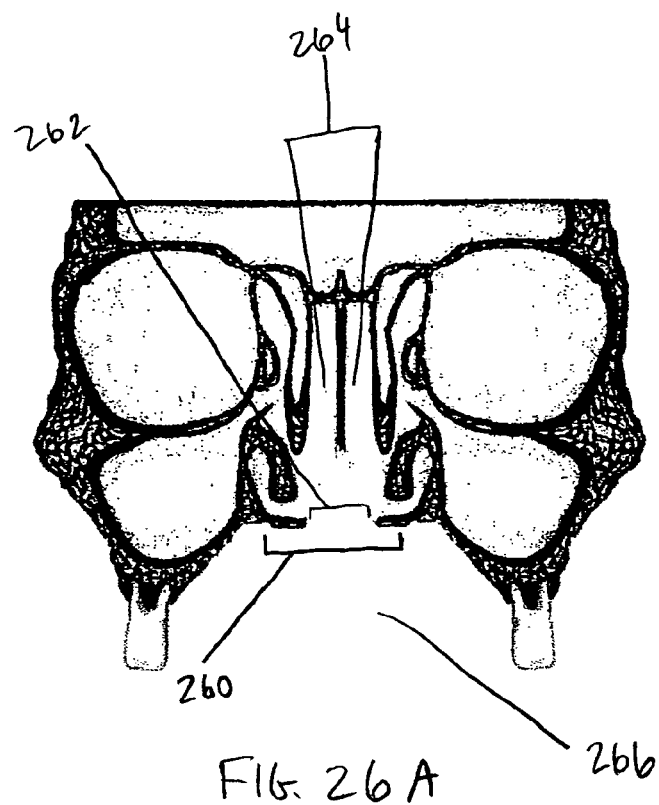
FIGS. 26A & 26B are diagrams that show the Bridge treating a bilateral cleft palate
Figure 26B:
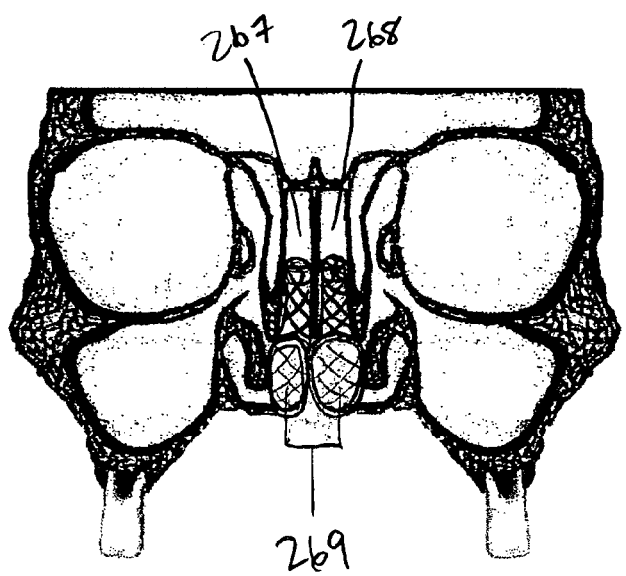

Similarly, FIG. 26 shows a bilateral cleft palate 260. This results in a fistula 262 that involves both nasal passages 264 and the oral cavity 266. In this situation, one Bridge 267 & 268) is placed in each nasal passage. The Bridges can be joined together by mechanical means such as sutures, dips and other means. They may also be constructed of magnetic or magnet materials. A plate can place in or on the palate and attached to the Bride if so required. This plate may be secured by magnetic means interacting with the Bridge(s) so that it can be easily removed if desired. After placement of the Bridge, the hard and/or soft palate can be attached to the Bridge if desired. The attachment means can be sutures, dips, staples, tacks, nails or other means. In all variations, the material can be partially or entirely made of materials that biodegrade and/or are bioabsorable. The axial through-lumens 269 of the Bridges allow for proper air exchange through the nose. The Bridge can provide a scaffold for tissue during reconstruction of the deft palate and deft lip. Likewise, one or more Bridge may be used to fixate fabric or tissue across the cleft fistula for a period long enough for the fabric or tissue to integrate with the native tissues, thus creating a patch. At this occurrence, the Bridge(s) may be removed.

Figure 27:
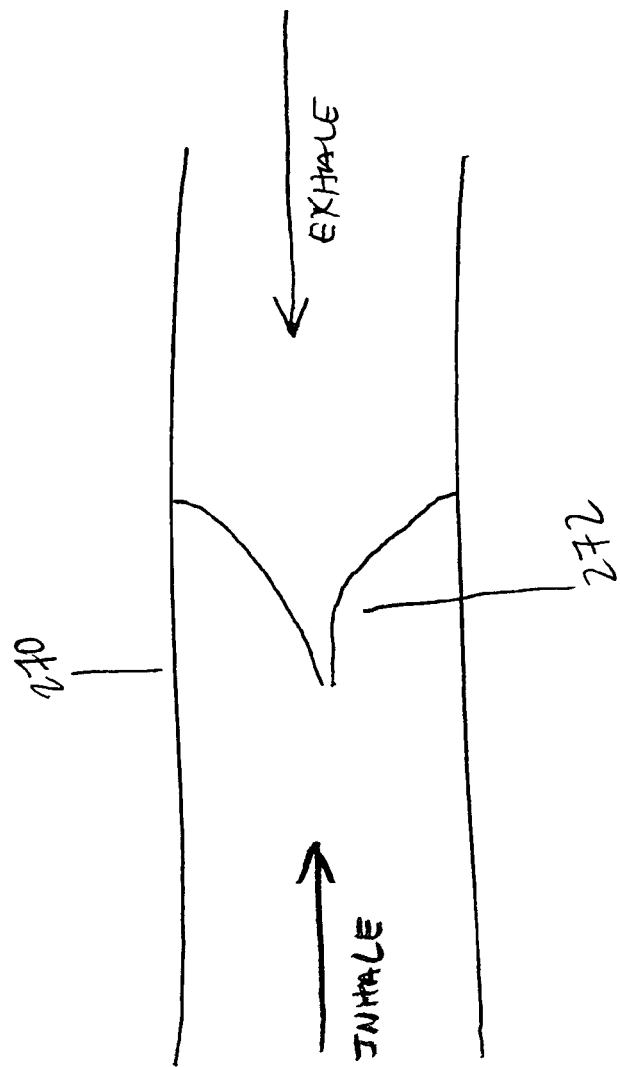
FIG. 27 shows a Bridge with a 1-way valve.

FIG. 27 shows a longitudinal cross-section view of a Bridge with a one-way valve 272. In this case, the valve design is a classic duck-bill form. It can be made of a soft material (e.g. silicone, polyurethane) so that it can contract and expand with the Bridge during processing and delivery. The soft material of the valve allows for devices such as a guidewire to pass through it to enable delivery. In this scenario, when implanted into the nasal or sinus passage, the valve prevents inhaled air to pass but allows exhaled air to pass. The orientation of the Bridge will determine air flow in and out of the nasal and sinus passages. This can help control contaminated air form entering the sinuses, or to balance the pressure across the cavities.

Figure 28:
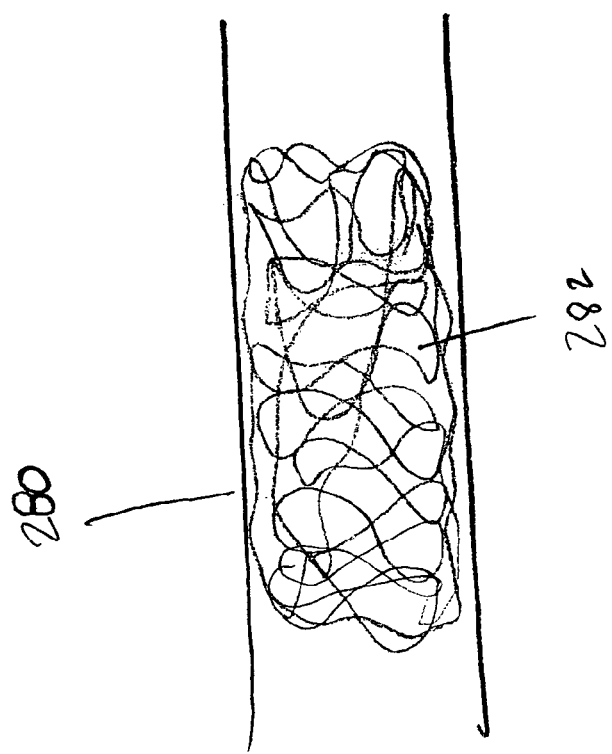
FIG. 28 shows a Bridge with filter media within the interior.

FIG. 28 shows a longitudinal cross-section view of a Bridge containing filter media 282. When the Bridge is implanted into a nasal or sinus passage, the filter 282 prevents contaminants form entering the sinuses. The filter can also be used to balance the pressure in the cavities. The filter media can be soft and pliable enough to allow for the passage of devices as well as allows the Bridge structure to expand or contact as needed.

Figure 29:
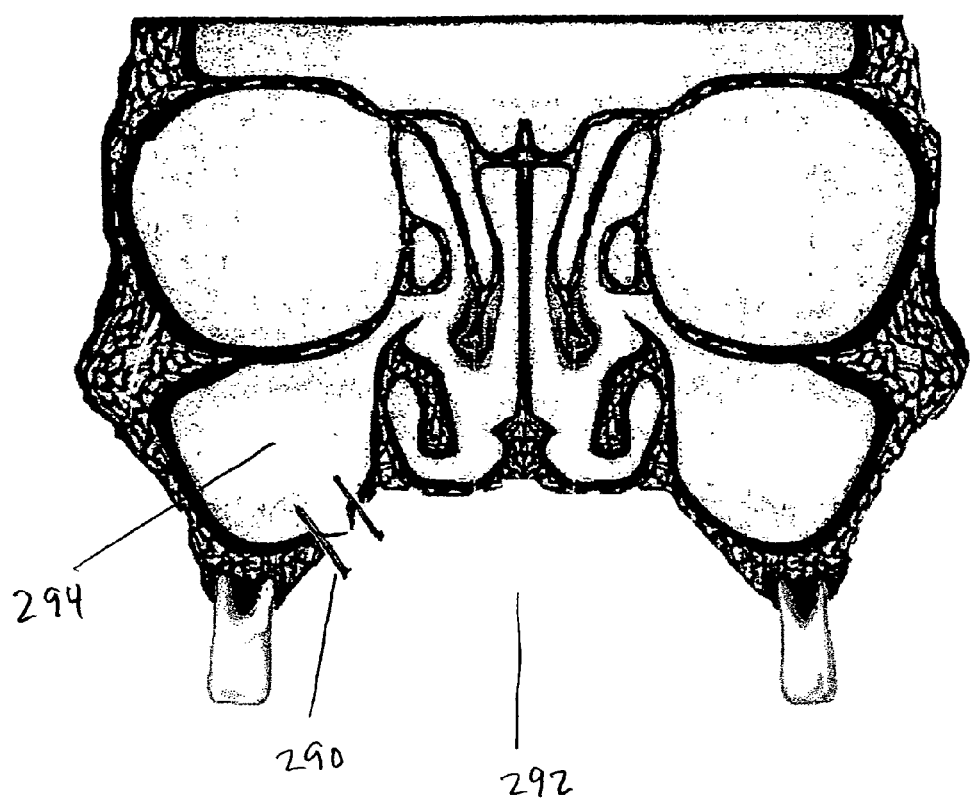
FIG. 29 shows a longitudal cross-section view of a Bridge with a one-way valve placed in between the oral cavity and the maxillary sinus.

FIG. 29 shows a longitudinal cross-section view of a Bridge with a one-way valve, similar to that in FIG. 27, placed in between the oral cavity and the maxillary sinus. The valve is oriented to allow for drainage into the oral cavity but prevent air or fluids form entering the sinus.

The treatment of these diseases is illustrative and is not meant to be limiting. With the foregoing detailed description of the present invention, it has been shown how the objects of the invention have been attained in a preferred manner. Modifications and equivalents of disclosed concepts such as those which might readily occur to one skilled in the art are intended to be included in the scope of the claims which are appended hereto.

What is claimed is:

1. A method of treating a sinus cavity of a patient comprising:
    traversing a passageway to the sinus cavity, wherein the passageway is through a tear duct;
    using endoscopy to guide a Bridge device through the passageway;
    viewing the sinus cavity with a visualization tool;
    positioning the Bridge device within the sinus cavity; and
    expanding the Bridge device within the sinus cavity.
2. The method of claim 1, wherein an inflatable balloon catheter causes the expansion of the Bridge device.
3. The method of claim 1, wherein the Bridge device is a tubular structure that, when compressed on its axis, expands radially and, dilates a constriction of the cavity.
4. The method of claim 1, wherein an inherent spring force contained within the Bridge device causes the expansion of the Bridge device.
5. The method of claim 1, wherein a self-contained portion within the Bridge device causes the expansion of the Bridge device.
6. The method of claim 1, wherein the Bridge device is tubular when expanded.
7. The method of claim 1, wherein the Bridge device has a covering.
8. The method of claim 1, wherein the Bridge device is coated with therapeutic agents.
9. A method of treating a constricted sinus cavity of a patient comprising:
    traversing a passageway through a tear duct to a sinus cavity;
    inserting an endoscope through the passageway;
    using the endoscope to guide a Bridge delivery system through the passageway;
    viewing the constricted sinus cavity with a visualization tool;
    positioning the Bridge delivery system within the constricted sinus cavity; and
    releasing a Bridge device within the constricted sinus cavity whereby the Bridge device dilates the constricted sinus cavity.
10. A method of treating a sinus cavity of a patient comprising:
    traversing a passageway to the sinus cavity, wherein the passageway is through a tooth;
    using endoscopy to guide a Bridge device through the passageway;
    viewing the sinus cavity with a visualization tool;
    positioning the Bridge device within the sinus cavity; and
    expanding the Bridge device within the sinus cavity.
11. The method of claim 10, wherein an inflatable balloon catheter causes the expansion of the Bridge device.
12. The method of claim 10, wherein the Bridge device is a tubular structure that, when compressed on its axis, expands radially and, dilates a constriction of the cavity.
13. The method of claim 10, wherein an inherent spring force contained within the Bridge device causes the expansion of the Bridge device.
14. The method of claim 10, wherein a self-contained portion within the Bridge device causes the expansion of the Bridge device.
15. The method of claim 10, wherein the expanded Bridge device is tubular.
16. The method of claim 10, wherein the Bridge device has a covering.
17. The method of claim 10, wherein the Bridge device is coated with therapeutic agents.

* * * * *